United States Patent
Hoke et al.

(10) Patent No.: US 10,925,820 B2
(45) Date of Patent: Feb. 23, 2021

(54) ORAL CARE COMPOSITIONS WITH AN EFFECTIVE FLAVOR DISPLAY

(71) Applicant: The Procter & Gamble Company, Cincinnati, OH (US)

(72) Inventors: Steven Hamilton Hoke, West Chester, OH (US); Sanjeev Midha, Mason, OH (US); Lawrence Edward Dolan, Cincinnati, OH (US); Michael Jude Leblanc, Cincinnati, OH (US); Karen Lehnhoff, Cincinnati, OH (US); Pierig Jean-Marie Lepont, Wyoming, OH (US); Jianjun Justin Li, West Chester, OH (US); Laura H. Lucas, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/475,168

(22) Filed: Mar. 31, 2017

(65) Prior Publication Data
US 2017/0281493 A1 Oct. 5, 2017

Related U.S. Application Data

(60) Provisional application No. 62/317,419, filed on Apr. 1, 2016, provisional application No. 62/317,415, filed on Apr. 1, 2016, provisional application No. 62/317,409, filed on Apr. 1, 2016, provisional application No. 62/317,413, filed on Apr. 1, 2016.

(51) Int. Cl.

| | |
|---|---|
| *A61Q 11/00* | (2006.01) |
| *A61K 8/21* | (2006.01) |
| *A61K 8/22* | (2006.01) |
| *A61K 8/00* | (2006.01) |
| *A61K 6/00* | (2020.01) |
| *A61K 8/18* | (2006.01) |
| *A61K 8/34* | (2006.01) |
| *A61Q 13/00* | (2006.01) |
| *A61K 8/02* | (2006.01) |
| *A61K 8/19* | (2006.01) |
| *A61K 8/31* | (2006.01) |
| *A61K 8/33* | (2006.01) |
| *A61K 8/35* | (2006.01) |
| *A61K 8/37* | (2006.01) |
| *A61K 8/49* | (2006.01) |

(52) U.S. Cl.
CPC ............ *A61K 8/342* (2013.01); *A61K 8/0216* (2013.01); *A61K 8/19* (2013.01); *A61K 8/21* (2013.01); *A61K 8/22* (2013.01); *A61K 8/31* (2013.01); *A61K 8/33* (2013.01); *A61K 8/34* (2013.01); *A61K 8/35* (2013.01); *A61K 8/37* (2013.01); *A61K 8/498* (2013.01); *A61Q 11/00* (2013.01); *A61Q 13/00* (2013.01); *A61K 2800/28* (2013.01)

(58) Field of Classification Search
CPC ... A61K 8/21; A61K 8/22; A61K 8/19; A61K 2800/92; A61K 2800/592
See application file for complete search history.

(56) References Cited

U.S. PATENT DOCUMENTS

| | | | |
|---|---|---|---|
| 4,666,517 A | 5/1987 | Bakar | |
| 5,093,112 A | 3/1992 | Birtwistle et al. | |
| 5,512,278 A | 4/1996 | Mundschenk | |
| 9,005,585 B2 | 4/2015 | Deckner et al. | |
| 2006/0034784 A1 | 2/2006 | Cahen et al. | |
| 2006/0210491 A1 | 9/2006 | Behan et al. | |
| 2009/0246151 A1* | 10/2009 | LeBlanc | A61K 8/0295 424/49 |
| 2012/0322709 A1 | 12/2012 | Li et al. | |
| 2013/0202746 A1* | 8/2013 | Siegel | A23L 1/22025 426/103 |
| 2014/0308322 A1 | 10/2014 | Midha et al. | |
| 2014/0336308 A1 | 11/2014 | Mateu et al. | |
| 2015/0023890 A1 | 1/2015 | Joziak et al. | |

FOREIGN PATENT DOCUMENTS

| | | | |
|---|---|---|---|
| DE | 4324859 A1 | 1/1994 | |
| EP | 0348560 A1 | 1/1990 | |
| WO | WO2008042279 A2 | 4/2008 | |
| WO | WO 2011053877 A2 * | 5/2011 | ............... A61K 8/22 |
| WO | WO2011053877 A2 | 5/2011 | |
| WO | WO2014169084 A1 | 10/2014 | |

OTHER PUBLICATIONS

U.S. Appl. No. 15/475,179, filed Mar. 31, 2017, Sanjeev Midha et al.
U.S. Appl. No. 15/475,172, filed Mar. 31, 2017, Sanjeev Midha et al.
U.S. Appl. No. 15/475,170, filed Mar. 31, 2017, Sanjeev Midha et al.
U.S. Appl. No. 15/475,169, filed Mar. 31, 2017, Sanjeev Midha et al.
International Search Report and Written Opinion for PCT/US2017/025237 dated May 23, 2017.

* cited by examiner

Primary Examiner — Tracy Liu
(74) Attorney, Agent, or Firm — Parker D. McCrary; Alexandra S. Anoff

(57) ABSTRACT

An oral care composition containing at least 4% fatty amphiphile and from about 0.4% to about 5%, by weight of the composition, total flavor components. The flavor components contain at least 14%, by weight of the flavor components, of one or more high displaying flavor components.

18 Claims, 2 Drawing Sheets

US 10,925,820 B2

ORAL CARE COMPOSITIONS WITH AN EFFECTIVE FLAVOR DISPLAY

FIELD OF THE INVENTION

The present invention relates to an oral care composition. More particularly a dentifrice composition with an effective flavor display.

BACKGROUND OF THE INVENTION

Oral care compositions, including dentifrice compositions, can contain fluoride salts, abrasives, and flavors to clean teeth, freshen breath, and maintain the aesthetics and health of the oral cavity, including the teeth and gums. It can be desirable to include a gel network phase as a structurant to help improve rheology and provide a unique brushing experience.

However, formulating a dentifrice composition that contains a fatty amphiphile, including a gel network, and an effective flavor display can be challenging, as fatty amphiphiles tend to suppress flavor display during brushing, reducing consumer satisfaction of the product.

As such, there is a need for an improved oral care composition that includes a fatty amphiphile and also delivers an effective flavor display.

SUMMARY OF THE INVENTION

An oral care composition comprising: (a) at least 4% fatty amphiphile; (b) from about 0.4% to about 5%, by weight of the composition, total flavor component; wherein the flavor component comprises at least 14%, by weight of the flavor component, of one or more high displaying flavor components; wherein the high displaying flavor components comprise an ACD vapor pressure greater than or equal to 0.06 Torr, a $\delta_P$ less than or equal to 5.3 MPa$^{1/2}$, and a $\delta_H$ of less than or equal to 7.0 MPa$^{1/2}$.

An oral care composition comprising: (a) at least 4% fatty amphiphile; (b) from about 0.4% to about 5%, by weight of the composition, total flavor component; wherein the flavor component comprises one or more high displaying flavor components comprising: (i) from about 4% to about 20%, by weight of the flavor component, anethole; (ii) from about 4% to about 30%, by weight of the flavor component, menthone.

An oral care composition comprising: (a) a gel network phase comprising at least 4% fatty amphiphile and a secondary surfactant; (b) from about 2% to about 25%, by weight of the composition, abrasive; (c) a fluoride ion source selected from the group consisting of stannous fluoride, sodium fluoride, potassium fluoride, amine fluoride, sodium monofluorophosphate, indium fluoride, amine fluoride, and combinations thereof; wherein the fluoride ion source provides a fluoride ion concentration from about 0.005% to about 2.0%, by weight of the composition; (d) from about 1% to about 90% water; (e) from about 0.4% to about 5%, by weight of the composition, total flavor component; wherein the flavor component comprises at least 14%, by weight of the flavor component, of one or more high displaying flavor components selected from the group consisting of anethole, eucalyptol, limonene, menthone, ethyl methyl butyrate, and combinations thereof.

DETAILED DESCRIPTION OF THE INVENTION

Figure 1:
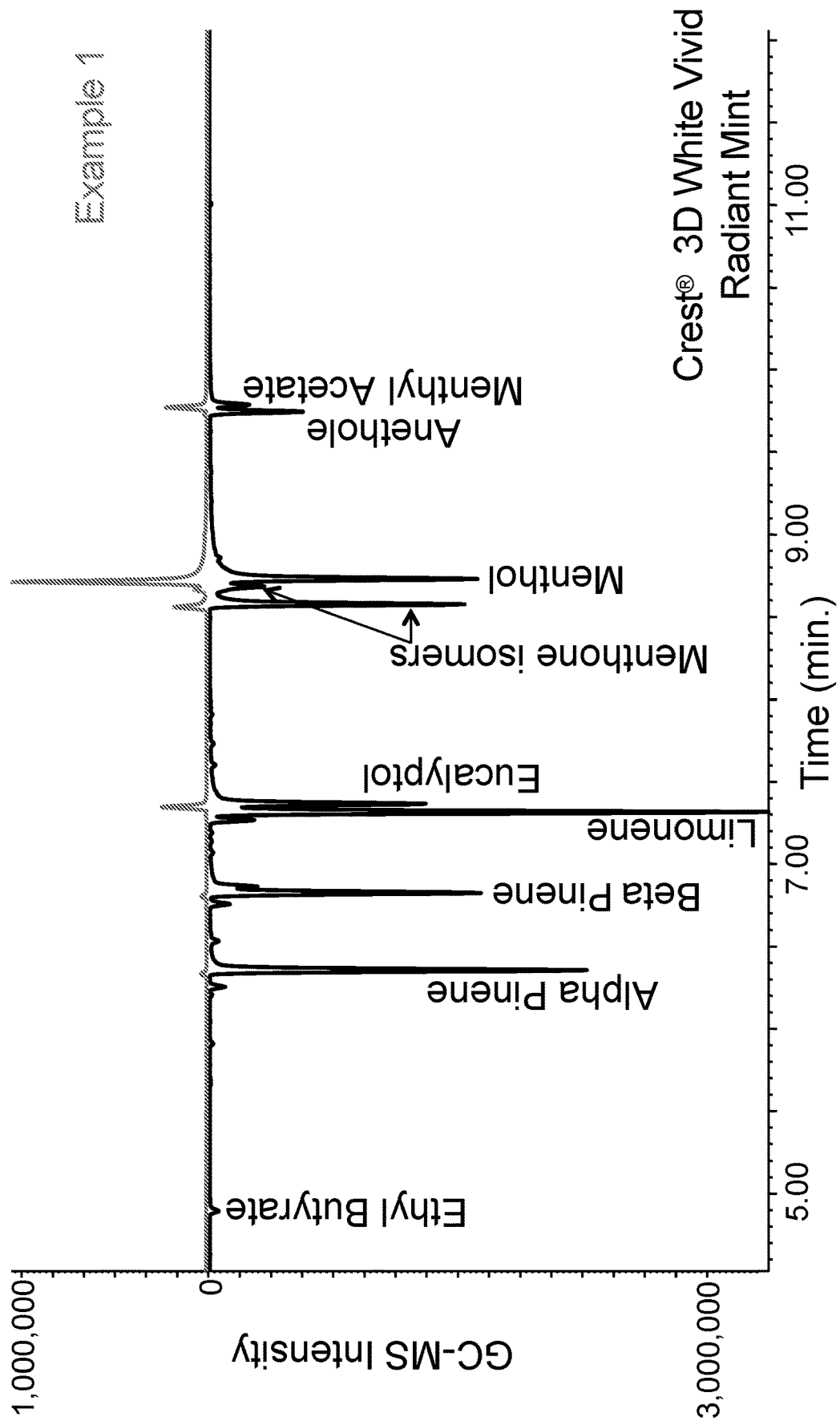
FIG. 1 shows the flavor display, as determined by gas chromatography-mass spectrometry (GC-MS) of Example 1 (top chromatogram) and Crest® 3D White Radiant Mint. (bottom chromatogram)

Dentifrice compositions can include fluoride, peroxide, pyrophosphate, potassium nitrate (KNO$_3$), abrasives, and/or other ingredients to provide benefits like reducing plaque and tartar, reducing pain from sensitive teeth, preventing cavities, preventing and reversing gingivitis, building protection against sensitivity, freshening bad breath, removing stains, and/or whitening teeth.

However, formulating toothpaste compositions with the proper rheology can be very challenging. The composition must not be too thick so it can easily dispense out of a tube but thick enough to stand up on a toothbrush without sinking into the bristles. The viscosity of the oral composition must remain stable over time as not to continue to thicken so the oral composition remains easy to dispense during the shelf life. Once dispensed from a container, the oral composition should not be stringy or sticky as to be messy for a consumer to use. The oral composition must also easily disperse once in the mouth and foam. It is also desired that the oral composition not stick to a sink or leave difficult to remove residue. In addition to balancing the viscosity and shear thinning to formulate acceptable rheology, the oral composition must also keep actives and other critical ingredients including fluoride salts, potassium nitrate, and/or peroxide stable and available.

One way to improve toothpaste rheology and stability is to include a gel network phase as a structurant. The gel network phase can include a fatty amphiphile, such as a fatty alcohol, and a secondary surfactant. A gel network phase can have other benefits including improving rheology and the gel network phase can also provide a unique brushing experience. For instance, dentifrice that contains a gel network phase can have excellent foaming and the foam may not easily break down during brushing, even when it is used with an electric toothbrush. Also, some commercially available dentifrices can feel harsh and can irritate a user's mouth, however, dentifrices containing gel networks can feel smooth and are generally non-irritating. Additionally, after brushing, the mouth not only feels fresh and clean, but a user's teeth can feel especially smooth and the smoothness can persist throughout the day because the amount of biofilm that builds on the teeth between brushings can be significantly reduced.

However, it has been observed that dentifrices containing a fatty amphiphile, including a gel network phase, tend to suppress flavor display during brushing, reducing overall consumer satisfaction of the product. These flavor display problems can be exacerbated when the dentifrice also contains one or more active and/or critical ingredients, including stannous fluoride, peroxide, and KNO$_3$. For instance, stannous fluoride can taste metallic, bitter, and astringent; peroxide, especially relatively high levels of peroxide, can have an off taste; and KNO$_3$ can have a salty and/or sour taste.

It can be tempting to boost flavor display by simply adding more flavor. However, there are practical limits to the amount of flavor that can be added to boost flavor impact. Flavors are one of the more expensive ingredients used in typical oral care compositions and so there are cost limitations. Additionally, high levels of flavor can cause oral soft tissue irritation.

Therefore, it can be desirable to include flavors that are particularly efficient at displaying in dentifrice compositions that contain fatty amphiphile and/or gel network phase to help mask these undesirable sensory experiences.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

The composition can contain, consist of, or consist essentially of, the essential elements and limitations of the invention described herein, as well as any additional or optional ingredients, components, or limitations described herein or otherwise useful in oral care compositions.

As used herein, the word "include," and its variants, are intended to be non-limiting, such that recitation of items in a list is not to the exclusion of other like items that may also be useful in the materials, compositions, devices, and methods of this invention.

As used herein, the articles "a" and "an" are understood to mean one or more of the material that is claimed or described, for example, "an abrasive" or "a surfactant".

As used herein, the word "or" when used as a connector of two or more elements is meant to include the elements individually and in combination; for example X or Y, means X or Y or both.

The term "flavor display", as used herein, refers to the volatilization of one or more flavor compounds from a composition upon mixing with water, saliva, and/or artificial saliva.

The term "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "effective amount" or "effective level" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount" means at least 0.01% of the material, by weight of the composition, alternatively at least 0.1%. In one example, an "effective level" of potassium nitrate can be about 5%.

The term "secondary surfactant" as used herein means a surfactant other than a fatty amphiphile. Various types of suitable surfactants are listed below. There may be more than one secondary surfactants. In one example, there can be at least one secondary surfactant in the gel network phase and there may be another surfactant in the oral carrier phase.

The term "teeth", as used herein, refers to natural teeth as well as artificial teeth or dental prosthesis.

The term "dentifrice", as used herein, includes tooth or subgingival paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side. As Herein, the terms "dentifrice" and "dentifrice" can be used interchangeably.

As used herein, the term "vapor pressure" means the partial pressure in air at a defined temperature for a given chemical species. It defines a chemical species' desire to be in the gas phase rather than the liquid or solid state. The higher the vapour pressure the greater the proportion of the material that will, at equilibrium, be found in a closed headspace. It is also related to the rate of evaporation of a flavor material which is defined in an open environment where material is leaving the system. The vapor pressure is determined according to the reference program Advanced Chemistry Development (ACD/Labs) Software Version 14.02, (© 1994-2015).

The term "water", as used herein, refers to deionized water, unless otherwise specified.

FIG. 1 shows the flavor display of Example 1 and Crest® 3D White Radiant Mint (purchased summer 2013). Example 1 is a dentifrice composition with a gel network phase, 3% hydrogen peroxide, and Tospearl® 145A (available from Momentive™ Performance Materials, New York, USA) as the abrasive (described in Table 1 and Table 2, below). The flavor aroma display over dentifrice slurry was evaluated by using the Flavor Aroma Display in Headspace over Dentifrice Slurry by GC/MS method sample preparation 1, 30 minute static headspace, as described hereafter.

TABLE 1

| Dentifrice Formulation for Example 1 | |
|---|---|
| Raw Material | Wt. % |
| Lanette ® W[1] | 11.8 |
| Sodium lauryl sulfate (SLS) Powder | 1.4 |
| Water | qs |
| Sodium fluoride | 0.243 |
| Sodium acid pyrophosphate | 0.3 |
| Disodium phosphate | 0.2 |
| Sucralose | 0.25 |
| Tospearl 145A[2] | 25 |
| Flavor Components - Example 1 (Table 2) | 2 |
| Hydrogen peroxide (35% solution) | 8.57 |
| Phosphoric acid | 0.10-0.15 |
| pH target => | 5.0-5.1 |

[1]Lanette ® W is mixture (40:40:10) of cetyl alcohol/stearyl alcohol/sodium lauryl sulfate and is available from BASF Corp.
[2]Polymethyl organosiloxane particles, more specifically polymethyl organosiloxane silicone resin particles, available from Momentive ™ Performance Materials, New York

TABLE 2

| Flavor Components - Example 1 | |
|---|---|
| Flavor Raw Material | Wt % |
| Dihydroanethole | 0.6 |
| Anethole | 5.0 |

TABLE 2-continued

Flavor Components - Example 1

| Flavor Raw Material | Wt % |
| --- | --- |
| Eucalyptol | 0.4 |
| Eugenol | 0.5 |
| Methyl salicylate | 3.5 |
| Menthol | 69.3 |
| Menthone | 4.0 |
| Methyl acetate | 5.9 |
| Propenyl guaethol | 0.8 |
| G180[3] (8%) in peppermint oil (92%) | 10.0 |

[3]Available from Givaudan (Cincinnati, Ohio)

Example 1 was made as follows. A jacketed mix tank was set to 85° C. Water and Lanette® W were added to the vessel under mixing until the temperature reached 80° C. SLS is added under agitation and the mixture was cooled to about 25° C., thus creating a gel network base. The mixture is cooled and vacuum de-aerated throughout cooling.

The powder ingredients including sodium fluoride, sodium acid pyrophosphate, sucralose, and abrasive were added to the gel network base. These were thoroughly mixed to approximate homogeneity and vacuum de-aerated to minimize air bubbles. The flavor was then thoroughly mixed into the batch. A small amount of phosphoric acid was added to achieve a the target pH. Following a final vacuum de-aeration step, the batch was transferred into standard tubes for evaluation.

The active ingredient in Crest® 3D White Vivid, Radiant Mint is sodium fluoride and the inactive ingredients include water, sorbitol, hydrated silica, disodium pyrophosphate, sodium lauryl sulfate, flavor, cellulose gum, sodium hydroxide, sodium saccharin, carbomer, xanthan gum, polyethylene, mica, titanium dioxide, and color. The flavor component level in Crest® 3D White Vivid, Radiant Mint is approximately 1.3%.

As shown in FIG. 1, Crest® 3D White display includes more peaks and generally larger peaks as compared to Example 1. Therefore, Crest® 3D White has a much more effective flavor display, this is surprising because Example 1 contains 2.0% flavor, which is far more (roughly double) the amount of flavor in Crest® 3D White. Furthermore, menthol and menthyl acetate, which contribute to the smell and flavor of peppermint, have peaks that are approximately the same size for both dentifrices. However, consumers generally prefer flavors that are more nuanced, which correlates to flavors that have more peaks and generally larger peaks as shown by GC-MS than Example 1. By examining the different components in FIG. 1, it was surprisingly found that not all of the flavor components were impacted by the dentifrice containing fatty amphiphile in the same way and some components displayed better than others.

In order to improve the flavor display in dentifrice compositions containing fatty amphiphiles, including gel networks, it was important to understand how common flavor components display in a dentifrice composition containing a gel network. Thus, a Model Flavor Accord, as described in Table 3 below, was used in Example 2A (1% Model Flavor Accord), Example 2B (2% Model Flavor Accord), and Example 2C (3% Model Flavor Accord). Examples 2A, 2B, and 2C are described in Table 4 below.

TABLE 3

Model Flavor Accord

| Flavor Raw Material | Wt. % |
| --- | --- |
| trans-Anethole | 4.00 |
| Cinnamic aldehyde | 3.00 |
| cis-3-hexen-1-ol | 2.00 |
| Eucalyptol | 3.00 |
| Guaiacol | 1.00 |
| Isoamyl acetate | 3.00 |
| (−)-carvone | 4.00 |
| (+)-limonene | 2.00 |
| 1-menthol | 33.00 |
| 1-Menthone | 5.00 |
| dl-Menthyl acetate | 4.00 |
| Methyl salicylate | 5.00 |
| Myrcene | 0.80 |
| Phenyl ethyl alcohol | 1.00 |
| Thymol | 0.60 |
| (−)-trans-caryophyllene | 1.00 |
| Beta-ionone | 1.00 |
| cis-jasmone | 3.00 |
| Neral | 2.00 |
| Piperitone | 2.00 |
| Ethyl methyl butyrate | 1.00 |
| Eugenol | 3.00 |
| Gamma undecalactone | 1.00 |
| Linalool | 2.00 |
| Melonal | 4.00 |
| Menthone Glycerol Acetal (MGA) | 3.00 |
| Oxanone | 1.00 |
| Vanillin | 0.60 |
| Vanillyl butyl ether | 2.00 |
| N-ethyl-p-menthan-3-carboxamide | 2.00 |

TABLE 4

Dentifrice Formulation for Examples 2A, 2B, and 2C

| Raw Material | 2A Wt. % | 2B Wt. % | 2C Wt. % |
| --- | --- | --- | --- |
| Lanette ® W[4] | 11.7 | 11.5 | 11.3 |
| Sodium Lauryl Sulfate (SLS) Powder | 1.5 | 1.4 | 1.4 |
| Water | qs | qs | qs |
| SLS Powder | 1.5 | 1.5 | 1.5 |
| Sodium fluoride | 0.243 | 0.243 | 0.243 |
| Sodium Acid Pyrophosphate | 0.3 | 0.3 | 0.3 |
| Disodium phosphate | 0.2 | 0.2 | 0.2 |
| Sucralose | 0.5 | 0.5 | 0.5 |
| Tospearl 145A[5] | 15 | 15 | 15 |
| Hydrogen peroxide (35% solution) | 8.57 | 8.57 | 8.57 |
| Flavor | 1 | 2 | 3 |
| Phosphoric Acid | 0.05-0.15 | 0.05-0.15 | 0.05-0.15 |
| pH target | 4.5-5.0 | 4.5-5.0 | 4.5-5.0 |

[4]Lanette ® W is mixture (40:40:10) of cetyl alcohol/stearyl alcohol/sodium lauryl sulfate and isavailable from BASF Corp.
[5]Polymethyl organosiloxane particles, more specifically polymethyl organosiloxane silicone resin particles, available from Momentive ™ Performance Materials, New York Examples 2A, 2B, and 2C were made according to the procedure described in Example 1.

Then, the Flavor Aroma Display in Headspace over Dentifrice Slurry by GC/MS Method Sample Preparation 2, 1 minute static headspace was performed, as described hereafter, to measure how the flavor accord displayed in Examples 2A, 2B, and 2C. N-ethyl-p-menthan-3-carboxamide, oxanone, MGA, and vanillyl butyl ether were not detected by this Method. Table 5 shows the average peak area for each flavor component per 100 ppm in dentifrice, based on triplicate analyses each of the 1%, 2% and 3% spiked flavor levels. Additionally, display efficiencies of each component was normalized to menthol by taking the Average Accord Peak Area/Concentration and dividing by the Average Accord Peak Area/Concentration for menthol. It was determined that menthol was a good flavor component to normalize against because menthol is commonly used in oral care formulations and was known to be at least an adequate displayer in oral care formulations. Table 5 is presented in order from the lowest to the highest efficiency displayers.

TABLE 5

Display Efficiency of Flavor Accord

| Flavor Compound | Avg. Peak Area/ 100 ppm in Dentifrice | Flavor Display Efficiency Normalized to Menthol | High, Medium or Low displayer |
|---|---|---|---|
| N-ETHYL-p-METHAN-3-CARBOXAMIDE (WS-3) | ND | NA | Low |
| OXANONE | ND | NA | Low |
| MGA | ND | NA | Low |
| VANILLYL BUTYL ETHER | ND | NA | Low |
| cis-JASMONE | 43.4 | 0.005 | Low |
| gamma UNDECALACTONE | 49.3 | 0.006 | Low |
| VANILLIN | 91.5 | 0.010 | Low |
| EUGENOL | 95.6 | 0.011 | Low |
| PHENYL ETHYL ALCOHOL | 257.3 | 0.029 | Low |
| NERAL | 268.2 | 0.031 | Low |
| CINNAMIC ALDEHYDE | 536.8 | 0.061 | Low |
| GUAICOL | 876.7 | 0.100 | Low |
| THYMOL | 1,732.3 | 0.198 | Medium |
| beta-CARYOPHYLLENE | 1,880.8 | 0.215 | Medium |
| beta-IONONE | 1,944.6 | 0.223 | Medium |
| cis-3-HEXEN-1-OL | 2,123.2 | 0.243 | Medium |
| PIPERITONE | 4,067.4 | 0.466 | Medium |
| METHYL SALICYLATE | 5,335.5 | 0.611 | Medium |
| CARVONE | 5,747.1 | 0.658 | Medium |
| l-MENTHOL | 8,730.3 | 1.000 | Medium |
| trans-ANETHOLE | 10,119.8 | 1.159 | High |
| LINALOOL | 10,357.1 | 1.186 | High |
| MYRCENE | 12,280.7 | 1.407 | High |
| MELONAL | 15,086.3 | 1.728 | High |
| LIMONENE | 19,770.8 | 2.265 | High |
| EUCALYPTOL | 27,915.1 | 3.197 | High |
| dl-MENTHYL ACETATE | 39,022.7 | 4.470 | High |
| l-MENTHONE | 40,124.4 | 4.596 | High |
| ISOAMYL ACETATE | 50,010.3 | 5.728 | High |
| ETHYL METHYL BUTYRATE | 56,476.2 | 6.469 | High |
| Total = | | | |

*ND = Not Detected, NA = Not Applicable

As shown in Table 5, menthol has a medium flavor display. However, there are some components such as trans-anethole, linalool, myrcene, melonal, limonene, eucalyptol, dl-menthyl acetate, l-menthone, isoamyl acetate, and ethyl methyl butyrate that have a surprisingly stronger flavor display in Example 2 and it may be advantageous to add more of these components to an oral care formulation in order to enhance the flavor display.

Additionally, it is important to balance the flavor profile. For instance, eucalyptol displays well in fatty amphiphile dentifrice and is commonly used in oral care products to impart fresh mint and/or spicy cooling. However, adding too much eucalyptol can cause the formulation to taste medicinal (e.g. like a cough drop), which does not deliver an optimal sensorial experience and may make a consumer feel like his/her breath is not fresh.

Based on the knowledge regarding the components that are high displayers in the Model Flavor Accord, additional flavor components were evaluated to determine which ones should also be high displayers based on the vapor pressure and individual Hansen Solubility Parameters (HSP) of a dispersion force component ($\delta_D$), a polar component ($\delta_P$), and a hydrogen bonding component ($\delta_H$), see Table 6 below. In Table 6, the flavor compound is considered a high displayer if the ACD vapor pressure was greater than or equal to 0.06 Torr, a $\delta_P$ less than or equal to 5.3 MPa$^{1/2}$ and a $\delta_H$ of less than or equal to 7.0 MPa$^{1/2}$. For all flavor components measured as high, medium, or low displayers in Table 5, these criteria provided for high displayers accurately predicts all 30 components as a high displayer or not in the Model Flavor Accord, with the exception of citral (geranial). This component exhibits notoriously poor stability, which may explain why its headspace peak area was lower than expected based on its ACD vapor pressure and Hansen solubility parameters.

Vapor pressure was calculated at 25° C. (unit, Torr) using the ACD/Lab model by Advanced Chemistry Development, Inc. (ACD/Labs, Toronto, Canada). Hansen Solubility Parameters (Dispersion, Polar, Hydrogen Bonding, all in unit of (MPa)$^{1/2}$) were computed using Steven Abbott and Hiroshi Yamamoto's "HSPIP—Hansen Solubility Parameters in Practice" program, 5$^{th}$ Edition, version 5.0.0.

TABLE 6

Classification of Flavor Display Efficiency in Fatty Amphiphile Dentifrice

| Flavor Compound | ACD 25° C. Vapor Pressure (Torr) | Dispersion ($\delta_D$) (MPa$^{1/2}$) | Polarity ($\delta_P$) (MPa$^{1/2}$) | Hydrogen Bonding ($\delta_H$) (MPa$^{1/2}$) | High Displayer in Fatty Amphiphile Dentifrice |
|---|---|---|---|---|---|
| ethyl methyl butyrate | 7.9E+00 | 15.59 | 3.82 | 4.92 | Y |
| isoamyl acetate | 3.9E+00 | 15.30 | 3.10 | 7.00 | Y |
| a-pinene | 3.5E+00 | 16.90 | 1.80 | 3.10 | Y |
| sabinene | 2.6E+00 | 16.58 | 1.52 | 1.77 | Y |
| b-pinene | 2.4E+00 | 16.23 | 0.95 | 1.78 | Y |
| myrcene | 2.3E+00 | 16.07 | 1.86 | 2.80 | Y |
| eucalyptol | 1.6E+00 | 16.70 | 4.60 | 3.40 | Y |
| a-terpinene | 1.6E+00 | 16.74 | 1.55 | 3.74 | Y |
| b-phellandrene | 1.6E+00 | 16.21 | 1.59 | 2.75 | Y |
| cis-ocimene | 1.6E+00 | 16.44 | 1.71 | 3.26 | Y |
| trans-ocimene | 1.6E+00 | 16.44 | 1.71 | 3.26 | Y |
| l-limonene | 1.5E+00 | 16.67 | 1.92 | 3.19 | Y |
| terpineolene | 1.1E+00 | 17.16 | 1.86 | 4.13 | Y |
| g-terpinene | 1.1E+00 | 16.60 | 1.69 | 3.68 | Y |
| cis-3-hexenol | 1.0E+00 | 16.58 | 5.67 | 11.12 | N |
| melonal | 6.2E−01 | 16.45 | 4.71 | 4.06 | Y |

TABLE 6-continued

Classification of Flavor Display Efficiency in Fatty Amphiphile Dentifrice

| Flavor Compound | ACD 25° C. Vapor Pressure (Torr) | Dispersion ($\delta_D$) (MPa$^{1/2}$) | Polarity ($\delta_P$) (MPa$^{1/2}$) | Hydrogen Bonding ($\delta_H$) (MPa$^{1/2}$) | High Displayer in Fatty Amphiphile Dentifrice |
|---|---|---|---|---|---|
| 3-octanol | 5.1E−01 | 15.96 | 4.13 | 8.90 | N |
| dihydroanethole | 2.7E−01 | 17.81 | 4.19 | 4.36 | Y |
| isomenthone | 2.6E−01 | 16.90 | 5.20 | 2.40 | Y |
| menthone | 2.6E−01 | 16.88 | 5.00 | 2.40 | Y |
| guaiacol | 1.8E−01 | 18.00 | 7.00 | 12.00 | N |
| peppermint cyclohexanone | 1.6E−01 | 16.85 | 3.93 | 2.03 | Y |
| cyclohexyl ethyl acetate | 1.5E−01 | 16.84 | 3.54 | 4.78 | Y |
| 5,6-dimethyl tetrahydropyran-2-one | 1.2E−01 | 16.37 | 7.73 | 4.97 | N |
| tetrahydrocarvone | 1.2E−01 | 16.88 | 5.00 | 2.40 | Y |
| D-dihydrocarvone | 1.1E−01 | 17.09 | 5.29 | 2.80 | Y |
| isopulegol | 9.9E−02 | 16.58 | 3.74 | 7.48 | N |
| pulegone | 9.3E−02 | 17.50 | 8.90 | 5.50 | N |
| linalool | 9.1E−02 | 16.76 | 2.89 | 6.94 | Y |
| sabinene Hydrate | 7.5E−02 | 17.45 | 4.24 | 5.91 | Y |
| phenyl ethyl alcohol | 7.4E−02 | 18.30 | 5.60 | 11.20 | N |
| citral | 7.1E−02 | 16.88 | 4.71 | 4.14 | Y |
| isomenthyl acetate | 7.1E−02 | 17.26 | 5.41 | 3.89 | N |
| 1-menthyl acetate | 7.1E−02 | 16.36 | 2.67 | 3.52 | Y |
| menthyl acetate | 7.1E−02 | 16.80 | 4.70 | 4.90 | Y |
| methyl salicylate | 7.0E−02 | 18.10 | 8.00 | 13.90 | N |
| anethole | 6.9E−02 | 18.50 | 4.30 | 6.00 | Y |
| trans anethole | 6.9E−02 | 18.44 | 4.47 | 5.05 | Y |
| d-carvone | 6.6E−02 | 17.47 | 5.81 | 3.73 | N |
| l-carvone | 6.6E−02 | 17.47 | 5.81 | 3.73 | N |
| 2'-4'-dimethyl acetophenone | 6.3E−02 | 18.53 | 6.23 | 1.14 | N |
| 2-cyclopentyl cyclopentanone | 5.9E−02 | 17.81 | 5.09 | 2.91 | N |
| piperitone | 5.7E−02 | 17.17 | 4.64 | 3.34 | N |
| terpinen-4-ol | 4.8E−02 | 17.26 | 4.05 | 7.15 | N |
| thujyl alcohol | 4.7E−02 | 16.75 | 3.72 | 6.77 | N |
| thymol | 3.8E−02 | 19.00 | 4.50 | 10.80 | N |
| isomenthol | 3.2E−02 | 17.50 | 10.36 | 2.87 | N |
| l-menthol | 3.2E−02 | 16.00 | 4.70 | 9.00 | N |
| neomenthol | 3.2E−02 | 17.50 | 10.36 | 2.87 | N |
| a-terpineol | 2.8E−02 | 17.03 | 3.58 | 7.66 | N |
| d-elemene | 2.8E−02 | 16.38 | 1.09 | 1.90 | N |
| methyl octalactone | 2.7E−02 | 16.22 | 10.43 | 4.11 | N |
| cinnamic aldehyde | 2.7E−02 | 18.72 | 6.69 | 5.42 | N |
| carvomenthol | 2.1E−02 | 16.45 | 3.51 | 6.91 | N |
| dihydrocarveol | 1.8E−02 | 16.58 | 3.74 | 7.48 | N |
| neodihydrocarveol | 1.8E−02 | 17.58 | 11.66 | 2.98 | N |
| beta-ionone | 1.7E−02 | 16.97 | 3.52 | 3.16 | N |
| b-caryophyllene | 1.3E−02 | 16.66 | 0.89 | 2.61 | N |
| cis-Carveol | 1.2E−02 | 16.92 | 3.84 | 8.44 | N |
| trans-Carveol | 1.2E−02 | 16.92 | 3.84 | 8.44 | N |
| eugenol | 1.0E−02 | 19.00 | 7.50 | 13.00 | N |
| delta damascone | 1.0E−02 | 16.89 | 3.48 | 2.61 | N |
| cis-Jasmone | 9.8E−03 | 17.76 | 4.73 | 4.73 | N |
| gamma nonalactone | 8.6E−03 | 16.46 | 11.03 | 4.86 | N |
| gamma decalactone | 8.5E−03 | 16.42 | 10.00 | 4.51 | N |
| delta decalactone | 8.3E−03 | 16.37 | 10.20 | 4.31 | N |
| a-humulene | 8.1E−03 | 17.01 | 1.57 | 3.92 | N |
| 5-pentyl-5H-furan-2-one | 7.3E−03 | 16.49 | 11.22 | 4.79 | N |
| germacrene-d | 6.7E−03 | 16.78 | 1.42 | 3.44 | N |
| caryophyllene oxide | 6.7E−03 | 16.73 | 2.48 | 2.15 | N |
| isoeugenol | 5.2E−03 | 18.88 | 5.71 | 9.79 | N |
| anisyl acetone | 3.8E−03 | 18.28 | 7.06 | 5.42 | N |
| gamma undecalactone | 2.7E−03 | 16.36 | 9.19 | 4.22 | N |
| 3-benzyl-4-heptanone | 2.1E−03 | 17.10 | 4.34 | 2.99 | N |
| vanillin | 1.9E−03 | 19.40 | 9.80 | 11.20 | N |
| delta dodecalactone | 1.6E−03 | 17.10 | 6.07 | 10.48 | N |
| carvyl acetate | 1.1E−03 | 16.81 | 2.70 | 4.24 | N |

TABLE 6-continued

Classification of Flavor Display Efficiency in Fatty Amphiphile Dentifrice

| Flavor Compound | ACD 25° C. Vapor Pressure (Torr) | Dispersion ($\delta_D$) (MPa$^{1/2}$) | Polarity ($\delta_P$) (MPa$^{1/2}$) | Hydrogen Bonding ($\delta_H$) (MPa$^{1/2}$) | High Displayer in Fatty Amphiphile Dentifrice |
|---|---|---|---|---|---|
| oxanone | 1.1E−03 | 18.71 | 7.61 | 9.72 | N |
| mint lactone | 9.1E−04 | 17.22 | 5.28 | 5.39 | N |
| ethyl vanillin | 8.8E−04 | 19.01 | 10.00 | 11.40 | N |
| apritone | 6.2E−04 | 17.50 | 4.02 | 2.55 | N |
| vanillyl butyl ether | 3.9E−04 | 17.93 | 5.65 | 8.17 | N |
| propenyl guaethol | 2.8E−04 | 18.51 | 5.39 | 9.06 | N |
| ethyl maltol | 2.3E−04 | 19.30 | 11.20 | 14.60 | N |
| WS-3 | 8.5E−05 | 17.09 | 7.27 | 4.07 | N |
| MGA | 2.2E−05 | 17.05 | 5.22 | 6.55 | N |

Therefore, in order to enhance flavor display in an oral care composition containing fatty amphiphiles, it can be advantageous to add higher displaying flavor components, including the components identified as high displayers in Table 6.

Figure 2:
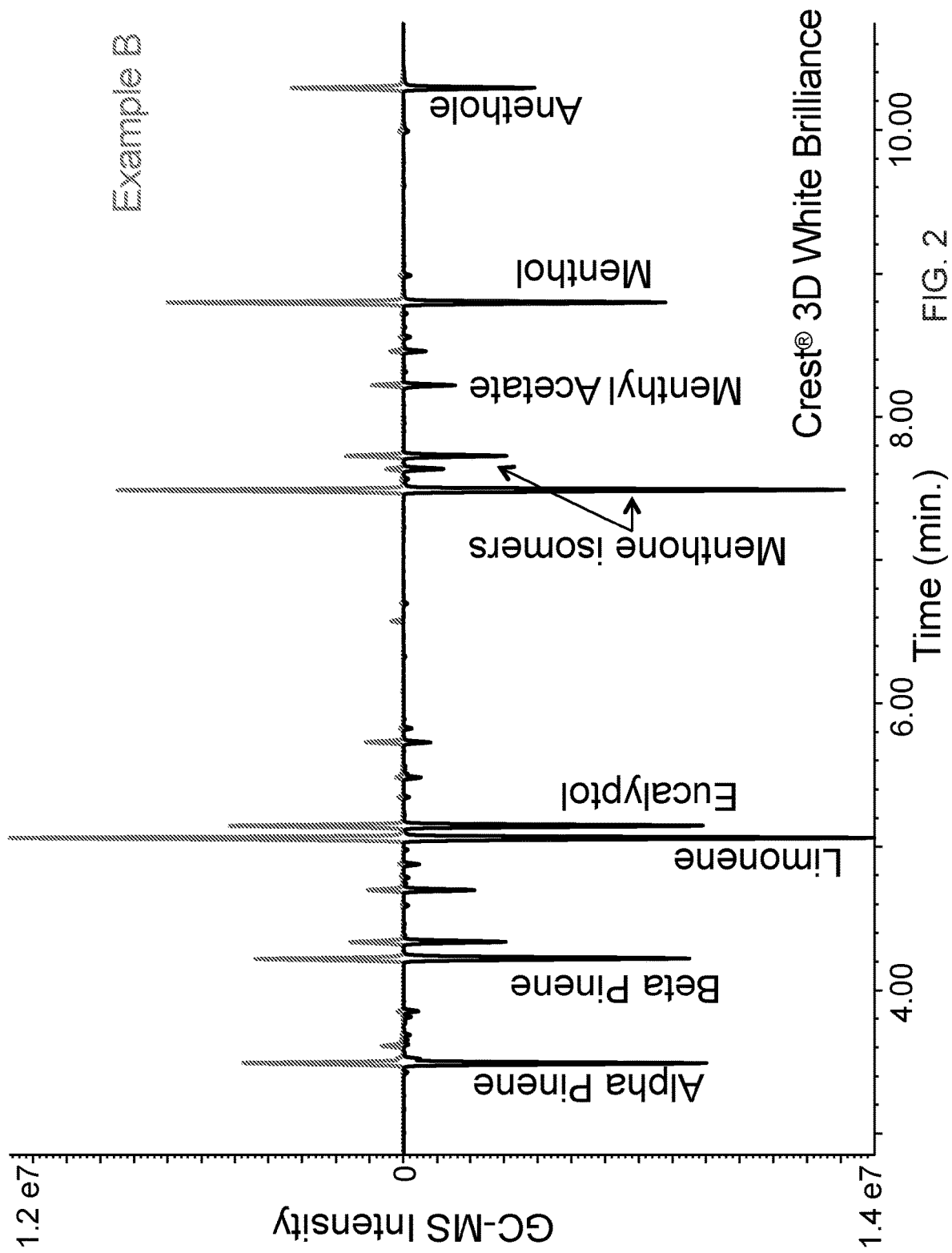
FIG. 2 shows the flavor display, as determined by gas chromatography-mass spectrometry (GC-MS) of Example B (top chromatogram) and Crest® 3D White Brilliance (bottom chromatogram).

Another flavor was made to increase the flavor display over Example 1. FIG. 2 shows the flavor display of Example B and Crest® 3D White Brilliance (Lot #6015GR). Example B is a dentifrice composition with a gel network phase, potassium nitrate, and a silica abrasive (described in Table 7, hereafter). The flavor display is determined by The Flavor in Headspace over Dentifrice Slurry by GC-MS Method 3, 1 minute SPME (solid phase microextraction), as described hereafter.

The active ingredient in Crest® 3D White Brilliance is sodium fluoride and the inactive ingredients include water, sorbitol, hydrated silica, disodium pyrophosphate, xylitol, flavor, sodium hydroxide, cellulose gum, cocamidopropyl betaine, sodium laureth-2 phosphate, sodium saccharin, xanthan gum, carbomer, sucralose, PEG-20M or PEG-23M, polyethylene, mica, titanium dioxide, and color. The flavor component level in Crest® 3D White Brilliance is approximately 1.3%.

As shown in FIG. 2, the flavor display, as demonstrated by the peaks in the chromatogram, for Crest® 3D White Brilliance are much more similar in intensity and diversity to Example B, compared with the poor display shown in FIG. 1, for Example 1. This demonstrates a step change improvement in flavor aroma display from a fatty amphiphile dentifrice. Therefore, the flavor of Example B is expected to deliver a much more refreshing and enjoyable brushing experience to consumers.

EXAMPLES

TABLE 7

Dentifrice Formulations for Examples A-D

| | Ex. A (wt. %) | Ex. B (wt. %) | Ex. C (wt. %) | Ex. D (wt. %) |
|---|---|---|---|---|
| Water | 53.32 | 16.47 | 51.89 | — |
| Lanette ® W[6] | 14.44 | — | 12.00 | 5.56 |
| Cold Dispersible Fatty Amphiphile[7] | — | 6.00 | — | — |
| Glycerin USP 99.7% Vegetable Base | — | — | — | 54.99 |
| Sorbitol Solution USP[8] | — | 41.10 | — | — |
| Saccharin Sodium USP Granular, High Moisture[9] | — | 0.45 | — | 0.45 |
| Sodium Lauryl Sulfate Powder | 4.13 | — | 2.50 | — |
| Sodium Lauryl Sulfate Solution (29%) | — | 9.50 | — | 3.40 |
| Cocamidopropyl Betaine Solution (30%) | — | 3.75 | — | — |
| Iota Carrageenan[10] | — | 0.30 | — | — |
| SepiMAX ™ ZEN[11] | — | — | 0.60 | — |
| Hydrogen Peroxide (35% Ultra Cosmetic) | 8.57 | — | 8.57 | — |
| Sodium Fluoride | 0.24 | 0.24 | 0.24 | — |
| Stannous Fluoride | — | — | — | 0.45 |
| Zinc Lactate Dihydrate | — | — | — | 2.50 |
| Sodium Polyphosphate Superfines | — | — | — | 13.00 |
| Sodium Gluconate | — | — | — | 0.65 |
| Sodium Acid Pyrophosphate | 0.60 | — | 0.50 | — |
| Dibasic Sodium Phosphate USP | 0.20 | — | 0.20 | — |
| Tribasic Sodium Phosphate Dodecahydrate | — | — | — | 1.10 |
| Sucralose | 0.50 | 0.25 | 0.50 | 0.05 |
| Potassium Nitrate USP | — | 5.00 | 5.00 | — |
| Tospearl ® 145A[12] | 15.00 | — | 15.00 | 15.00 |
| Zeodent ® 119[13] | — | 15.00 | — | — |
| Titanium Dioxide USP | — | — | — | 0.75 |
| Flavor Components | 3.00 | 1.74 | 3.00 | 2.10 |
| Sodium Hydroxide Solution (50%) Food Chemical Codex | — | 0.20 | — | — |

[6]Lanette ® W is mixture (40:40:10) of cetyl alcohol/stearyl alcohol/sodium lauryl sulfate and is available from BASF Corp
[7]The cold dispersible fatty amphiphile is 40% cetyl alcohol, 40% stearyl alcohol, 10% sodium lauryl sulfate, and 10% sodium acrylate/sodium acryloyl dimethyl daurate copolymer.
[8]Sorbitol Solution USP is an aqueous solution containing 70% sorbitol
[9]Saccharin Sodium USP Granular, high moisture contains up to 14% water
[10]Iota Carrageenan contains approximately 5% silica as a processing aid (commercially available from FMC Health and Nutrition (USA))
[11]Polyacrylate crosspolymer-6, available from SEPPIC S.A.
[12]Polymethyl organosiloxane particles, more specifically polymethyl organosiloxane silicone resin particles, available from Momentive ™ Performance Materials, New York
[13]Available from J. M. Huber Corporation (Edison, New Jersey)

Table 8, below, summarizes the high displaying flavor components in Examples A-D. The high displaying flavor components have an ACD vapor pressure greater than or equal to 0.06 Torr, an $\delta_P$ less than or equal to 5.3 MPa$^{1/2}$ and a $\delta_H$ of less than or equal to 7.0 MPa$^{1/2}$.

TABLE 8

High Displaying Flavor Components in Examples A-D

| | Example A | Example B | Example C | Example D |
|---|---|---|---|---|
| High Displayers Measured in Dentifrice (ppm)[14] | 4,453 | 5,933 | 4,394 | 7,360 |
| High Displayers Measured in Dentifrice (%)[14] | 0.445 | 0.593 | 0.439 | 0.736 |
| High Displayers in Flavor Formulation (%)[14] | 14.8 | 34.1 | 14.6 | 35.0 |
| High Displayers in Headspace After Simulated Brushing (% Peak Area)[15] | 51.7 | 85.9 | 53.3 | 77.7 |

[14]The high displayers in dentifrice and flavor formulation (%) were determined using the Quantification of Percent Flavor in Gel Network Dentifrice by GC-MS, described hereafter.
[15]The high displayers in headspace after simulated brushing (the peak area arising from high displaying flavor components divided by the total peak area arising from all flavor components expressed as a percentage) is found using the Flavor Aroma Display in Headspace over Dentifrice Slurry by GC/MS method sample preparation 3, 1 minute SPME, as described hereafter.

Examples A, C, and D were made as follows. A jacketed mix tank was set to 85° C. Water or glycerin and Lanette® W were added to the vessel with agitation until the temperature reached 80° C. and a solution that includes melted fatty alcohols and SLS was formed. Then, the heating jacket was reset to 25° C. and the batch was cooled and polyacrylate crosspolymer-6 (if present) was added. After the mixture cools, the following materials were added to the vessel: potassium nitrate (if present), sodium fluoride, sodium acid pyrophosphate, dibasic sodium phosphate, and sucralose with agitation and homogenization. Next, the abrasive (Tospearl® 145A) was added to the vessel with agitation and the mixture was thoroughly mixed. Once the abrasive had wetted out (i.e. no powders are floating on top of the liquid) the mixture was deaerated. Once the composition was approximately homogenous and approximately all of the air was removed the flavor was added to the vessel with agitation. The mixture was then deaerated again. Finally, the first bit of heterogeneous material was removed at the beginning of pumping out of mix tank into a separate container and was discarded as scrap. Once the material began to appear homogeneous, it was collected in a clean container and stored as the final composition. The final composition can then be used to fill tubes, if desired.

Example B was made as follows. A jacketed mix tank was set to 30° C. The water, 0.1% SLS, and sorbitol solution were added to the vessel with homogenization. Then, the carrageenan was slowly added and then the cold dispersible fatty amphiphile was added under agitation to form a substantially homogenous mixture. Then, the following materials were added to the vessel: saccharine, sucralose, sodium fluoride, sodium hydroxide solution, and potassium nitrate with agitation and homogenization. Then, the abrasive (Zeodent® 119) was added to the vessel with agitation. Once the abrasive had wetted out, the mixture was deaerated. Once the composition was approximately homogenous and approximately all of the air was removed, the remaining SLS, cocamidopropyl betaine solution, and flavor were added to the vessel with agitation. The mixture was then deaerated again. Next, a sample was removed and the pH was measured. In examples where pH adjustment was needed sodium hydroxide solution was added until the composition reached the target pH and the mixture was deaerated again. Finally, the first bit of heterogeneous material was removed at the beginning of pumping out of mix tank into a separate container and was discarded as scrap. Once the material began to appear homogeneous, it was collected in a clean container and stored as the final composition. The final composition can then be used to fill tubes, if desired.

Here, flavor components are defined as including both traditional flavor compounds as well as sensates. Examples of some traditional flavor compounds that may be used in oral care compositions are mint oils, and components thereof, wintergreen, clove bud oil, cassia, sage, parsley oil, marjoram, lemon, orange, propenyl guaethol, heliotropine, cis-4-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, isopulegol, piperitone, or combinations thereof. Generally suitable flavoring ingredients are chemicals with structural features and functional groups that are less prone to redox reactions. These include derivatives of flavor chemicals that are saturated or contain stable aromatic rings or ester groups.

Sensates may also be part of an oral care composition that are intended to deliver a desirable consumer experience. Sensate molecules such as cooling, warming, and tingling agents are useful to deliver signals to the user. Even though sensates are generally not high displayers, it can be desirable to include them because they can play an important role, especially in providing a cooling effect after brushing. Sensates are generally present in an amount of from about 0.001% to about 2%, by weight of the oral care composition, alternatively from about 0.01% to about 1.75%, alternatively 0.1% to about 1.5%, and alternatively 0.5% to about 1.25%. The most well-known cooling sensate compound can be menthol, particularly L-menthol, which is found naturally in peppermint and spearmint oils notably of *Mentha piperita*, *Mentha arvensis* L and *Mentha viridis* L. Other isomers of menthol (neomenthol, isomenthol and neoisomenthol) have somewhat similar, but not identical odor and taste, and may have, for instance, disagreeable odor and taste notes described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there can be no cooling effect for the other isomers. For example, d-neomenthol is reported to have a cooling threshold of about 25,000 ppb and l-neomenthol about 3,000 ppb.

Of the menthol isomers the l-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5

(N-ethoxycarbonylmethyl-ρ-menthan-3-carboxamide), WS-12 (1R*,2S*)—N-(4-Methoxyphenyl)-5-methyl-2-(1-methylethyl)cyclohexanecarboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425 to Amano et al. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)p-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,917, 613; 3,991,178; 5,703,123; 5,725,865; 5,843,466; 6,365, 215; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630 and phosphine oxides as reported in U.S. Pat. No. 4,070,496.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethyl vanillyl alcohol alkyl ethers; veratryl alcohol derivatives; substituted benzyl alcohol derivatives; substituted benzyl alcohol alkyl ethers; vanillin propylene glycol acetal; ethyl vanillin propylene glycol acetal; ginger extract; ginger oil; gingerol; zingerone; or combinations thereof. Warming sensates are generally included in an oral care composition at a level of about 0.05% to about 2%, by weight of the oral care composition.

Flavor components can be present in an amount of from about 0.4% to about 5%, by total weight of the oral care composition, in another example from about 0.8% to about 4%, in another example from about 1% to about 3.5%, and in another example from about 1.5% to about 3%. It can be desirable to have a flavor composition at less than about 4%, less than about 3.5%, by total weight of the oral care composition, in another example less than about 3%, and in another example less than about 2%.

The oral care composition can contain one or more flavor components that are high displaying flavor components. A flavor component can be a high displaying flavor component if it has an ACD vapor pressure greater than or equal to 0.06 Torr, an $\delta_P$ less than or equal to 5.3 MPa$^{1/2}$ and a $\delta_H$ of less than or equal to 7.0 MPa$^{1/2}$.

The oral care composition can contain one or more high displaying flavor components selected from the group consisting of ethyl methyl butyrate, isoamyl acetate, alpha-pinene, sabinene, beta-pinene, myrcene, eucalyptol, alpha-terpinene, beta-phellandrene, cis-ocimene, trans-ocimene, l-limonene, terpineolene, g-terpinene, melonal, dihydroanethole, isomenthone, menthone, peppermint cyclohexanone, cyclohexyl ethyl acetate, tetrahydrocarvone, d-dihydrocarvone, linalool, sabinene hydrate, citral, l-menthyl acetate, menthyl acetate, anethole, trans anethole, and combinations thereof. The oral care composition can contain one or more high displaying flavor components selected from the group consisting of anethole, eucalyptol, limonene, menthone, alpha pinene, beta pinene, ethyl methyl butyrate, and combinations thereof.

The oral care composition can contain at least 0.02% of high displaying flavor components, by weight, of the composition, alternatively at least 0.07%, alternatively at least 0.1%, alternatively at least 0.15%, alternatively at least 0.2%, alternatively at least 0.25%, alternatively at least 0.3%, alternatively at least 0.4%, alternatively at least 0.42%, alternatively at least 0.43%, alternatively at least 0.44%, alternatively at least 0.5%, alternatively at least 0.55%, alternatively at least 0.58%, alternatively at least 0.63%, alternatively at least 0.67%, alternatively at least 0.7%, and alternatively at least 0.72%. The oral care composition can contain from about 0.03% to about 2% of high displaying flavor components, by weight, of the composition, alternatively from about 0.04% to about 1.8%, alternatively from about 0.06% to about 1.5%, alternatively from about 0.08% to about 1.2%, alternatively from about 0.1% to about 1%, alternatively from about 0.16% to about 0.8%, alternatively from about 0.22% to about 0.7%, alternatively from about 0.28% to about 0.66%, alternatively from about 0.34% to about 0.6%, alternatively from about 0.38% to about 0.57%, and alternatively from about 0.42% to about 0.52%.

The flavor components can contain at least 5% of high displaying flavor components, by weight, of the total flavor components, alternatively at least 8%, alternatively at least 10%, alternatively at least 12%, alternatively at least 13%, alternatively at least 14%, alternatively at least 15%, alternatively at least 20%, alternatively at least 25%, alternatively at least 30%, alternatively at least 33%, alternatively at least 35%, alternatively at least 40%, alternatively at least 45% and/or at least 50%. The total flavor components can contain from 1% to 70% of high displaying flavor components, by weight of the total flavor components, alternatively from about 3% to about 60%, alternatively from about 7% to about 50%, from about 10% to about 45%, alternatively from about 12% to about 40%, alternatively from about 14% to about 38%, and alternatively from about 20% to about 30%. The amount of high displaying flavor components in the total flavor component and/or the oral care composition can be determined using Quantification of Percent Flavor in Gel Network Dentifrice by GC-MS, as described hereafter.

After simulated brushing, as described hereafter in Flavor Aroma Display in Headspace over Dentifrice Slurry by GC/MS method 3, 1 minute SPME, the oral care composition can have from about 20% to about 95% high displayers in the headspace, alternatively from about 30% to about 90%, alternatively from about 40% to about 88%, alternatively from about 45% to about 86%, alternatively from about 50% to about 80%, and alternatively from about 55% to about 75%. After simulated brushing the oral care composition can have at least 10% high displayers in the headspace, alternatively at least 20%, alternatively at least 30%, at least 40%, alternatively at least 45%, alternatively at least 50%, alternatively at least 55%, alternatively at least 60%, alternatively at least 70%, alternatively at least 75%, alternatively at least 80%, and alternatively at least 84%.

The flavor component can contain anethole. The flavor component can contain from about 1% to about 40% anethole, by weight of the total flavor component, alternatively from about 3% to about 25%, alternatively from about 4% to about 20%, alternatively from about 5% to about 15%, alternatively from about 7% to about 13%, and alternatively from about 9% to about 12%. The oral care composition can contain from about 0.001% to about 1% anethole, by weight of the oral care composition, alternatively from about 0.005% to about 0.7%, alternatively from about 0.01% to about 0.5%, alternatively from about 0.05% to about 0.4%, alternatively from about 0.1% to about 0.35%, alternatively from about 0.15% to 0.25%, alternatively greater than 0.2%, alternatively greater than 0.5%. Alternatively, the flavor can be substantially free of anethole.

The flavor component can contain limonene. The flavor component can contain limonene The flavor component can contain from about 0.1% to about 10% limonene, by weight of the total flavor component, alternatively from about 0.25% to about 7%, alternatively from about 0.5% to about 5%, and alternatively from about 1% to about 3%. The oral care composition can contain from about 0.001% to about 0.5% limonene, by weight of the oral care composition, alternatively from about 0.003% to about 0.3%, alternatively from about 0.04% to about 0.2%, alternatively from about 0.05% to about 0.1%, alternatively greater than 0.01%, greater than 0.03%, alternatively greater than 0.05%, alternatively greater than 0.1%, greater than 0.2%. Alternatively, the flavor component can be substantially free of limonene.

The flavor component can contain eucalyptol. The flavor component can contain from about 0.1% to about 10% eucalyptol, by weight of the total flavor component, alternatively from about 0.25% to about 7%, alternatively from about 0.5% to about 5%, and alternatively from about 1% to about 3%. The oral care composition can contain from about 0.001% to about 0.5% eucalyptol, by weight of the oral care composition, alternatively from about 0.003% to about 0.3%, alternatively from about 0.04% to about 0.2%, alternatively from about 0.05% to about 0.1%, alternatively greater than 0.01%, alternatively greater than 0.03%, alternatively greater than 0.05%, alternatively greater than 0.1%, and alternatively greater than 0.2%. Alternatively, the flavor component can be substantially free of eucalyptol.

The flavor component can contain menthone. The flavor component can contain from about 1% to about 50% menthone, by weight of the total flavor component, alternatively from about 3% to about 30%, alternatively from about 4% to about 20%, alternatively from about 5% to about 18%, alternatively from about 7% to about 16%, and alternatively from about 10% to about 14%. The oral care composition can contain from about 0.001% to about 2% menthone, by weight of the oral care composition, alternatively from about 0.005% to about 1.5%, alternatively from about 0.01% to about 1%, alternatively from about 0.05% to about 0.7%, alternatively from about 0.1% to about 0.5%, alternatively from about 0.15% to 0.5%, alternatively greater than 0.2%, alternatively greater than 0.5%, and alternatively greater than 0.7%. Alternatively, the flavor can be substantially free of menthone.

The flavor component can contain ethyl methyl butyrate. The flavor component can contain from about 0.1% to about 10% ethyl methyl butyrate, by weight of the total flavor component, alternatively from about 0.25% to about 7%, alternatively from about 0.5% to about 5%, and alternatively from about 1% to about 3%. The oral care composition can contain from about 0.001% to about 0.5% ethyl methyl butyrate, by weight of the oral care composition, alternatively from about 0.003% to about 0.3%, alternatively from about 0.04% to about 0.2%, alternatively from about 0.05% to about 0.1%, alternatively greater than 0.01%, alternatively greater than 0.03%, alternatively greater than 0.05%, alternatively greater than 0.1%, and alternatively greater than 0.2%. Alternatively, the flavor component can be substantially free of ethyl methyl butyrate.

The flavor component can contain alpha pinene. The flavor component can contain from about 0.05% to about 5% alpha pinene, by weight of the total flavor component, alternatively from about 0.15% to about 3%, alternatively from about 0.25% to about 1.5%, and alternatively from about 0.5% to about 1%. The oral care composition can contain from about 0.001% to about 0.25% alpha pinene, by weight of the oral care composition, alternatively from about 0.003% to about 0.15%, alternatively from about 0.04% to about 0.1%, alternatively from about 0.025% to about 0.05%, alternatively greater than 0.01%, alternatively greater than 0.03%, alternatively greater than 0.025%, alternatively greater than 0.05%, and alternatively greater than 0.1%. Alternatively, the flavor component can be substantially free of alpha pinene.

The flavor component can contain beta pinene. The flavor component can contain from about 0.05% to about 5% beta pinene, by weight of the total flavor component, alternatively from about 0.15% to about 3%, alternatively from about 0.25% to about 1.5%, and alternatively from about 0.5% to about 1%. The oral care composition can contain from about 0.001% to about 0.25% beta pinene, by weight of the oral care composition, alternatively from about 0.003% to about 0.15%, alternatively from about 0.04% to about 0.1%, alternatively from about 0.025% to about 0.05%, alternatively greater than 0.01%, alternatively greater than 0.03%, alternatively greater than 0.025%, alternatively greater than 0.05%, and alternatively greater than 0.1%. Alternatively, the flavor component can be substantially free of beta pinene.

It can be desirable to have non-high displaying flavor components in the formulation. The non-high displaying flavor components can help balance the overall flavor display and consumer experience. A non-high displaying flavor component can be any flavor component that is not a high-displaying flavor component including but not limited to l-menthol, methyl salicylate, carvone, and combinations thereof.

The oral care composition can contain from about 0.1% to about 3% of non-high displaying flavor components, by weight of the composition, alternatively from about 0.25% to about 2.5%, alternatively from about 0.5% to about 2%, alternatively from about 0.7% to about 1.5%, alternatively from about 0.8% to about 1.25%, alternatively greater than 1%, alternatively greater than 1.5%.

The total flavor components can contain from about 10% to about 99% non-high displaying flavor components, by weight of the total flavor components, alternatively from about 15% to about 95%, alternatively from about 18% to about 90%, alternatively from about 22% to about 90%, alternatively from about 25% to about 85%, alternatively from about 30% to about 80%, alternatively from about 35% to about 70%, alternatively from about 40% to about 60%, and alternatively from about 45% to about 55%.

The flavor component can contain l-menthol. The flavor component can contain from about 1% to about 70% l-menthol, by weight of the total flavor component, alternatively from about 5% to about 60%, alternatively from about 10% to about 50%, alternatively from about 20% to about 45%, alternatively from about 25% to about 40%, and alternatively from about 32% to about 38%. Alternatively, the flavor component can contain from about 10% to about 75% l-menthol, by weight of the total flavor component, alternatively from about 25% to about 65%, alternatively from about 40% to about 60%, alternatively from about 50% to about 57%. The oral care composition can contain from about 0.001% to about 3% l-menthol, by weight of the oral care composition, alternatively from about 0.05% to about 2%, alternatively from about 0.1% to about 1.7%, alternatively from about 0.3% to about 1.5%, alternatively from about 0.5% to about 1.25%, alternatively from about 0.75% to 1.15%, alternatively greater than 0.5%, alternatively greater than 0.75%, alternatively greater than 1%, alternatively greater than 1.25%, alternatively greater than 1.5%. Alternatively, the flavor can be substantially free of l-menthol.

The flavor component can contain methyl salicylate. The flavor component can contain from about 1% to about 60% methyl salicylate, by weight of the total flavor component, alternatively from about 5% to about 50%, alternatively from about 10% to about 40%, alternatively from about 15% to about 35%, alternatively from about 20% to about 30%, and alternatively from about 22% to about 28%. The oral care composition can contain from about 0.001% to about 2% methyl salicylate, by weight of the oral care composition, alternatively from about 0.05% to about 1.75%, alternatively from about 0.1% to about 1.5%, alternatively from about 0.3% to about 1.25%, alternatively from about 0.5% to about 1%, alternatively from about 0.6% to 0.9%, alternatively greater than 0.25%, alternatively greater than 0.6%, alternatively greater than 0.75%, alternatively greater than 1%, alternatively greater than 1.25%, alternatively greater than 1.5%. Alternatively, the flavor can be substantially free of methyl salicylate.

The flavor component can contain carvone. The flavor component can contain from about 1% to about 60% carvone, by weight of the total flavor component, alternatively from about 5% to about 50%, alternatively from about 10% to about 40%, alternatively from about 15% to about 35%, alternatively from about 20% to about 30%, and alternatively from about 22% to about 28%. The oral care composition can contain from about 0.001% to about 2% l-carvone, by weight of the oral care composition, alternatively from about 0.05% to about 1.75%, alternatively from about 0.1% to about 1.5%, alternatively from about 0.3% to about 1.25%, alternatively from about 0.5% to about 1%, alternatively from about 0.6% to 0.9%, alternatively greater than 0.25%, alternatively greater than 0.6%, alternatively greater than 0.75%, alternatively greater than 1%, alternatively greater than 1.25%, alternatively greater than 1.5%. Alternatively, the flavor can be substantially free of carvone.

The flavor component can contain fruit oils selected from the group consisting of lime oil, orange oil, pineapple oil, and combinations thereof. The flavor component can contain from about 0.01% to about 60% fruit oil, by weight of the total flavor component, alternatively from about 0.05% to about 40%, alternatively from about 0.07% to about 30%, alternatively from about 0.1% to about 15%, alternatively from about 0.15% to about 10%, alternatively from about 0.2% to about 5%, alternatively from about 0.1% to about 1%, alternatively from about 0.25% to about 0.75%. The oral care composition can contain from about 0.0001% to about 4% fruit oil, by weight of the oral care composition, alternatively from about 0.0003% to about 3%, alternatively from about 0.0005% to about 1.5%, alternatively from 0.001% to about 1%, and alternatively from about 0.01% to about 0.5%.

The flavor component can contain pineapple flavoring. The flavor component can contain from about 0.01% to about 40% pineapple flavoring, by weight of the total flavor component, alternatively from about 0.05% to about 30%, alternatively from about 0.07% to about 15%, alternatively from about 0.1% to about 10%, alternatively from about 0.15% to about 5%, alternatively from about 0.2% to about 3%, alternatively from about 0.1% to about 1%, alternatively from about 0.25% to about 0.75%. The oral care composition can contain from about 0.0001% to about 4% pineapple flavor, by weight of the oral care composition, alternatively from about 0.0003% to about 3%, alternatively from about 0.0005% to about 1.5%, alternatively from 0.001% to about 1%, and alternatively from about 0.01% to about 0.5%.

As used herein, "fatty amphiphile" refers to a compound having a hydrophobic tail group and a hydrophilic head group which does not make the compound water soluble (immiscible), wherein the compound also has a net neutral charge at the pH of the oral composition. The fatty amphiphile can be selected from the group consisting of fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxylated amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, phospholipids, and combinations thereof. Suitable fatty amphiphiles include a combination of cetyl alcohol and stearyl alcohol. The fatty amphiphile can be a fatty alcohol.

The fatty amphiphile can be a fatty alcohol. The fatty amphiphiles can include a cetyl alcohol and/or stearyl alcohol. The oral care compositions may contain a fatty amphiphile in an amount greater than about 2%, alternatively greater than about 4%, alternatively greater than about 5%, alternatively greater than alternatively about 7.5%, alternatively greater than about 10%, alternatively greater than about 11%, alternatively greater than about 13%, alternatively greater than about 14%, alternatively greater from about 14.5%, alternatively greater than about 15%, alternatively greater than about 15.5%, alternatively greater than about 16%. The oral care composition may contain a fatty amphiphile in an amount less than about 40%, alternatively less than about 35%, less than about 30%, alternatively less than about 25%, alternatively less than about 22%, alternatively less than about 20%, alternatively less than about 19%, alternatively less than about 18%, alternatively less than about 17%. The oral care composition may contain a fatty amphiphile in an amount from about 3% to about 30%, alternatively from about 4% to about 28%, alternatively from about 5% to about 26%, alternatively from about 7% to about 25%, alternatively from about 8% to about 23%, alternatively from about 10% to about 21%, alternatively from about 12% to about 20%, alternatively from about 13% to about 19%, alternatively from about 14% to about 18%, alternatively from about 15% to about 17%.

The total flavor can be adjusted based on the amount of fatty amphiphile in the composition. For instance, an oral care composition that contains from about 9% to about 12% fatty amphiphile and the composition can contain from about 2.0% to about 4% total flavor component and a composition that contains from about 3% to about 6% fatty amphiphile may contain less than 2.5% total flavor component or from about 1.5% to about 2.4% total flavor component.

The toothpaste can be phase stable and can contain a gel network phase, which can include a cold dispersible fatty amphiphile and the composition can contain less than about 14% fatty amphiphile.

The composition can contain a cold dispersible fatty amphiphile. The composition can contain from about 1% to about 20% cold dispersible fatty amphiphile, alternatively from about 3% to about 17%, alternatively from about 5% to about 15%, alternatively from about 7% to about 13%, alternatively from about 8% to about 12%, and alternatively from about 9% to about 11.5%. The composition can contain from about 0.1% to about 5% cold dispersible fatty amphiphile, alternatively from about 0.5% to about 3%, alternatively from about 0.75% to about 2.5%, and alternatively from about 1% to about 2%. The composition can contain greater than about 0.5% cold dispersible fatty amphiphile, alternatively greater than about 1%, alternatively greater than about 3%, alternatively greater than about 5%, alternatively greater than about 7%, alternatively greater than about 8%, and alternatively greater than about 9%.

The cold dispersible fatty amphiphile can have a melting point greater than about 10° C., alternatively greater than about 25° C., alternatively greater than about 30° C., alternatively greater than about 35° C., alternatively greater than about 40° C., alternatively greater than about 45° C., alternatively greater than about 55° C. The melting point of the cold dispersible fatty amphiphile can be from about 20° C. to about 100° C., alternatively from about 30° C. to about 90° C., alternatively from about 35° C. to about 85° C., alternatively from about 40° C. to about 80° C., alternatively from about 45° C. to about 75° C., alternatively from about 50° C. to about 70° C., alternatively from about 55° C. to about 65° C., and alternatively from about 57° C. to about 67° C. Melting point can be determined by USP (United States Pharmacopeia) Testing Method <741>, Class 1a, Apparatus I.

The cold dispersible fatty amphiphile can contain straight or branched carbon chains from about C8 to about C25 and from about C12 to about C22.

The cold dispersible fatty amphiphile can contain 40% cetyl alcohol, 40% stearyl alcohol, 10% sodium lauryl sulfate (SLS), and 10% sodium acrylate/sodium acryloyl dimethyl taurate copolymer.

The composition of the cold dispersible fatty amphiphile can contain from about 40% to about 98% fatty amphiphile, alternatively from about 50% to about 95% alternatively fatty amphiphile, alternatively from about 60% to about 90% fatty amphiphile, alternatively from about 70% to about 85% fatty amphiphile, and alternatively from about 75% to about 80% fatty amphiphile. The fatty amphiphile can be a fatty alcohol. The cold dispersible fatty amphiphile can contain one fatty alcohol and/or fatty amphiphile, alternatively two different fatty alcohols and/or fatty amphiphile, alternatively three different fatty alcohols and/or fatty amphiphile, alternatively four different fatty alcohols and/or fatty amphiphiles, and alternatively five or more different fatty alcohols and/or fatty amphiphiles. The cold dispersible fatty amphiphile can contain a fatty alcohol selected from the group consisting of cetyl alcohol, stearyl alcohol, and combinations thereof. The cold dispersible fatty amphiphile can contain two fatty alcohols where the first fatty alcohol is cetyl alcohol and the second fatty alcohol is stearyl alcohol. The ratio of first fatty amphiphile to second fatty amphiphile can be about 1:5 to about 5:1, alternatively from about 1:4 to about 4:1, alternatively from about 1:3 to about 3:1, alternatively from about 1:2 to about 2:1, and alternatively the ratio can be about 1:1.

The cold dispersible fatty amphiphile can contain from about 1% to about 40% surfactant, alternatively from about 5% to about 30%, alternatively from about 7% to about 20%, and alternatively from about 10% to about 15%. The surfactant can be an anionic surfactant. The surfactant can be sodium lauryl sulfate.

The cold dispersible fatty amphiphile can contain from about 1% to about 40% polymer, alternatively from about 5% to about 30%, alternatively from about 7% to about 20%, alternatively from about 8% to about 15%, alternatively from about 9% to about 14%, alternatively from about 10% to about 12%.

The oral care composition can contain one or more secondary surfactants. The secondary surfactant is typically water soluble or miscible in the solvent or oral carrier. Suitable secondary surfactants include anionic, zwitterionic, amphoteric, cationic, and nonionic secondary surfactants. Anionic secondary surfactants can contain sodium lauryl sulfate. The composition can contain a total amount of secondary surfactant from about 1% to about 15%, alternatively from about 2% to about 12%, alternatively from about 3% to about 11%, alternatively from about 4% to about 10.5%, alternatively from 5% to about 9.75%, alternatively from about 7% to about 9.5%, and alternatively from about 8% to about 9.5%. The composition can include a secondary surfactant as part of the cold dispersible fatty amphiphile and a secondary surfactant that is not part of the cold dispersible fatty amphiphile. The composition can contain 1% to 10% secondary surfactant that is not part of the cold dispersible fatty amphiphile, alternatively from about 2% to about 7%, and alternatively from about 3% to about 6%. The secondary surfactants may be a combination of more than one type of secondary surfactants, such as an anionic and nonionic secondary surfactant. Suitable solvents for the present invention can include water, edible polyhydric alcohols such as glycerin, diglycerin, triglycerin, sorbitol, xylitol, butylene glycol, erythritol, polyethylene glycol, propylene glycol, and combinations thereof.

Secondary surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, and can be selected from linear or branched, alkyl or alkenyl group of from 1 to 22 carbon atoms, optionally substituted by one or more phosphate groups; alkoxylated alkyl or alkenyl, (poly)saccharide, polyol or polyether group.

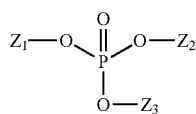

Some other organophosphate agents include alkyl or alkenyl phosphate esters represented by the following structure:

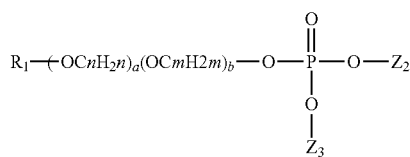

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a (OCmH2m)b- group. Suitable agents can include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. The alkyl phosphate can be polymeric. Polymeric alkyl phosphates can include those containing repeating alkoxy groups as the polymeric portion, in particular 3 or more ethoxy, propoxy isopropoxy or butoxy groups.

Zwitterionic or amphoteric secondary surfactants useful in the present invention can include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric secondary surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N, N-dimethyl ammonio) acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these secondary surfactants are soapy, bitter, chemical, or artificial. The composition can contain from about 0.1% to about 6% amphoteric secondary surfactant, alternatively from about 0.5% to about 4%, alternatively from about 0.75% to about 2%, alternatively from about 1% to about 1.5%.

Additional suitable polymeric organophosphate agents can include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic secondary surfactants useful in the present invention can include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421 to Briner et al. Certain cationic secondary surfactants can also act as germicides in the oral care compositions disclosed herein.

The oral care composition can have a viscosity from about 5 BKUs to about 70 BKUs, alternatively from about 10 BKUs to about 45 BKUs, alternatively from about 12 BKUs to about 40 BKUs, alternatively from about 15 BKUs to about 35 BKUs, alternatively from about 18 BKUs to about 30 BKUs, alternatively from about 20 BKUs to about 28 BKUs, and alternatively from about 22 BKUs to about 25 BKUs. The oral care compositions can have a viscosity from about 10 BKUs to about 200 BKUs, alternatively from about 20 BKUs to about 175 BKUs, alternatively from about 30 BKUs to about 150 BKUs, alternatively from about 50 BKUs to 100 BKUs. Viscosity can measured by the Brookfield Viscosity Test as described hereafter.

The oral care composition can have a shelf life, when stored below 40° C., of at least 6 months, alternatively at least 1 year, alternatively at least 18 months, alternatively at least 2 years, alternatively at least 30 months, and alternatively at least 3 years. The shelf life can be from about 6 months to about 5 years, alternatively from about 1 year to about 3 years, and alternatively from about 1.5 years to about 2.5 years.

The oral care composition can have a pH from about 2 to about 10, alternatively from about 4 to about 9, alternatively from about 5 to about 8, and alternatively from about 6 to about 7.5 pH can be measured using the pH Test Method as described hereafter.

Actives and other ingredients (including critical ingredients) may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

It is common to have a fluoride compound present in toothpastes and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 to Briner et al. and U.S. Pat. No. 3,678,154 to Widder et al.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the oral care composition. Some metal salts which may be used in the present invention, such as zinc chloride, zinc citrate, copper gluconate, and zinc gluconate, are also associated with an off taste described as dirty, dry, earthy, metallic, sour, bitter, and astringent.

Stannous salts include stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients used to stabilize the stannous may be included, such as the ingredients described in Majeti et al. and Prencipe et al.

Zinc salts include zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof.

The copper salt can be selected from copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. The copper salt can be selected from copper gluconate, copper acetate, copper glycinate, and combinations thereof.

Sweeteners can include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

Rebiana can be a steviolglycoside from Cargill Corp., Minneapolis, Minn., which is an extract from the leaves of the *Stevia rebaudiana* plant (hereinafter referred to as "Rebiana"). This is a crystalline diterpene glycoside, about 300× sweeter than sucrose. Suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable examples of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials can include water, glycerin, sorbitol, polyethylene glycols including those having a molecular weight of less than about 50,000, propylene glycol and other edible polyhydric alcohols, ethanol, or combinations thereof. The oral care compositions of the present invention include from about 5% to about 80%, by weight of the composition, of a carrier material. The compositions can contain carrier materials in an amount of from about 10% to about 40%, by total weight of the oral care composition.

The composition can contain from about 15% to about 95% water, alternatively from about 20% to about 85%, alternatively from about 25% to about 70%, alternatively from about 28% to about 60%, alternatively from about 30% to about 50%, alternatively from about 31% to about 48%, alternatively from about 32% to about 45%, and alternatively from about 33% to about 43%. The composition can contain from about 1% to about 20% water, alternatively from about 2% to about 15% water, alternatively from about 3% to about 10% water, and alternatively from about 4% to about 8% water. The composition can contain greater than about 5% water, alternatively greater than about 8%, alternatively greater than about 10%, alternatively greater than about 15%, alternatively greater than about 20%, alternatively greater than about 25%, alternatively greater than about 30%, alternatively greater than about 40%, and alternatively greater than about 50%.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Pyridinium quaternary ammonium compounds can include bis[4-(R-amino)-1-pyridinium] alkanes as disclosed in U.S. Pat. No. 4,206,215, Jun. 3, 1980, to Bailey and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, and flavor oils such as thymol. In another example, the antimicrobial agent can include triclosan.

Thickening material or binders may be used to provide a desirable consistency to the oral care compositions of the present invention.

Thickening materials can include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. The thickening material can be carrageenan. Thickening materials can be used in an amount from about 0.1% to about 15%, by weight of the oral care composition. Thickening materials can be used in an amount from about 0.01% to about 3%, alternatively from about 0.1% to about 2%, alternatively from about 0.2% to about 1%, alternatively from about 0.25% to about 0.75%, alternatively from about 0.27% to about 0.5%, and alternatively from about 0.3% to about 0.4%. The oral care compositions can also contain binders that can also adjust formulation texture and mouth feel.

The thickening agent can include the addition of polymers of acrylic acid crosslinked with an unsaturated polyfunctional agent such as a polyallyl ether of sucrose. These carboxy vinyl polymers have the CTFA (Cosmetic, Toiletry and Fragrance Association) adopted name of "carbomer." A carbomer can include negatively charged polyelectrolytes, such as Carbomer 956 (available from Lubrizol Corporation, Wickliffe, Ohio). The carbomer can be selected from the group consisting of acrylates/C10-30 alkyl acrylate crosspolymer, sodium polyacrylate; polyacrylate-1 Crosspolymer (available from Lubrizol); polyacrylate Crosspolymer-11 (available from Clariant, Inc., Louisville, Ky., USA), acrylates/C10-30 alkyl acrylate crosspolymer, and combinations thereof. The carbomer can be Carbomer 956. The composition can contain from about 0.1% to about 15% carbomer, alternatively from about 0.3% to about 10% carbomer, alternatively from about 0.5% to about 6% carbomer, alternatively from about 0.7% to about 3% carbomer, and alternatively from about 0.9% to about 1.5% carbomer. Examples of additional carbomers can be found in U.S. Pat. No. 2,798,053.

In some oral care compositions, for instance examples that contain peroxide, it is not desirable to include certain polymers because they will not be stable. The oral care composition can be substantially free of carrageenan. The composition can be substantially free of carboxymethyl cellulose. The composition can be substantially free of xanthan gum. In the oral care composition can contain an AMPS polymer, co-polymer, and/or crosspolymer, as described above. Non-limiting examples of polymers, copolymers and crosspolymers synthesized from AMPS can include hydroxyethyl acrylate/sodium acryloyldimethyl taurate copolymer (commercially available as Sepinov™ EMT-10 from SEPPIC S.A.), ammonium acryloyldimethyl taurate/vinyl pyrrolidone copolymer (commercially available as Aristoflex® AVC from Clariant International LTD, Muttenz, Switzerland), ammonium acryloyldimethyltaurate/beheneth-25 methacrylate crosspolymer (commercially available as Aristoflex® HMB, Clariant International LTD), sodium acrylate/sodium acryloyldimethyltaurate copolymer (a component of Sepigel EG and Simulgel SMS 88, SEPPIC S.A.), acrylamide/sodium acryloyldimethyltaurate copolymer (a component of Simulgel 600 and Simulgel 600 PHA, SEPPIC S.A.), polyacrylate crosspolymer-6 (commercially available as SepiMAX™ ZEN from SEPPIC S.A.), and combinations thereof.

The oral care composition can contain polyacrylate crosspolymer-6 (commercially available as SepiMAX™ ZEN from SEPPIC S.A., a subsidiary of the Air Liquide group, Puteaux Cedex, France). The molecular structure of polyacrylate crosspolymer-6 is shown below.

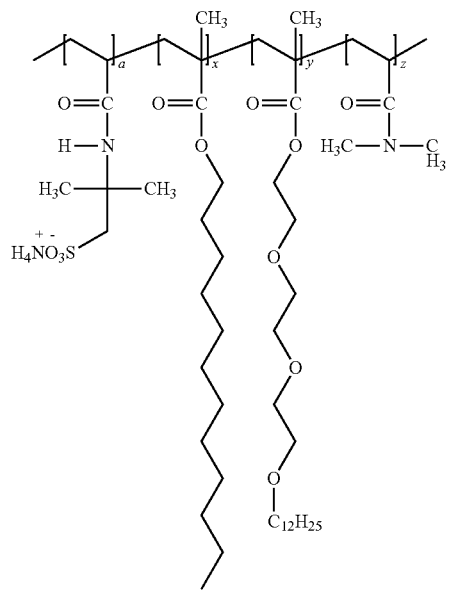

Polyacrylate crosspolymer-6 is a copolymer of Ammonium 2-methyl-2-[(1-oxo-2-propenyl)amino]-1-propanesulfonate, N,N Dimethyl-2-acrylamide, Poly(oxy-1,2-ethanediyl), alpha-(2-methyl-1-oxo-2-propenyl0-omega-(dodecyloxy) and Methyl-2-propenoic acid dodecyl ester monomers.

The oral care composition can contain from about 0.1% to about 10% AMPS polymer, copolymer, or crosspolymer, alternatively from about 0.5% to about 7%, alternatively from about 1% to about 5%, alternatively from about 1.2% to about 4%, and alternatively from about 1.6% to about 3.5%. The oral care composition can contain from about 0.01% to about 5% AMPS polymer, copolymer, or crosspolymer, in another example from about 0.1% to about 3%, alternatively from about 0.25% to about 1.5%, alternatively from about 0.3% to about 1%, and alternatively from about 0.5% to about 0.8%.

The compositions of the present invention may contain antimicrobial agents in an amount of from about 0.035% or more, from about 0.1% to about 2.0%, from about 0.045% to about 1.0%, or from about 0.05% to about 0.10%, by total weight of the oral care composition. Alternatively from about 0.001% to about 1.5% antimicrobial agent, alternatively from about 0.005% to about 0.8%, alternatively from 0.01% to about 0.7%, alternatively from about 0.05% to about 0.5%, and alternatively from about 0.1% to about 0.3%.

Non-limiting examples of peroxide (peroxygen) compounds can include hydrogen peroxide, urea peroxide, calcium peroxide, sodium peroxide, zinc peroxide, polyvinylpyrrolidone peroxide complex or combinations thereof. The composition can contain greater than about 0.05% peroxide, alternatively greater than about 0.5% peroxide, alternatively greater than about 0.75%, alternatively greater than about 1%, alternatively greater than about 1.25%, in alternatively greater than about 1.5%, alternatively greater than about 1.75%. alternatively greater than about 2%, alternatively greater than about 2.25%, alternatively greater than about 2.5%, alternatively greater than about 2.75%, alternatively greater than about 2.85%, alternatively greater than about 2.9%, alternatively greater than about 2.95%, alternatively greater than about 3%, alternatively greater than about 4%, alternatively greater than about 5%, and alternatively greater than about 6%. The composition can contain from about 0.01% to 10% peroxide, alternatively from about 0.05% to about 8%, alternatively from about 0.1% to about 5%, alternatively 0.5% to about 4.5%, alternatively 1% to about 4%, alternatively about 1.5% to about 3.5%, and alternatively about 2% to about 3%. The composition can contain from about 1% to about 10% peroxide, alternatively from about 2% to about 8% peroxide, alternatively from about 3% to about 7% peroxide, and alternatively from about 4% to about 6% peroxide. The composition can contain from about 0.01% to about 6% peroxide, alternatively from about 0.05% to about 3%, and alternatively from about 0.1% to about 1%.

The composition can be free of or substantially free of a peroxide component.

The oral care composition can include bleaching agents. Bleaching agents can include perborates, percarbonates, peroxyacids, persulfates, and combinations thereof. One example of a percarbonate is sodium percarbonate. An example of a persulfate includes oxones. Some bleaching agents provide a burn sensation within an oral care composition, for example peroxides and percarbonates.

The compositions of the present invention may contain bleaching agents in an amount of from about 0.01% to about 30%, from about 0.1% to about 10%, or from about 0.5% to about 5%, by total weight of the oral care composition.

Dentifrice compositions of the present invention may also comprise an anti-calculus agent, which may be present from about 0.05% to about 50%, by weight of the dentifrice composition, alternatively from about 0.05% to about 25%, and alternatively from about 0.1% to about 15%. The compositions can contain an amount of anti-calculus agent that is effective in tartar control effective. The amount of pyrophosphate salt may be from about 1.5% to about 15%, alternatively from about 2% to about 10%, or alternatively from about 3% to about 8%. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. The salts can be alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. The composition can contain from about 1% to about 30% polyphosphate salts, alternatively from about 5% to about 25%, alternatively from about 10% to about 20%, alternatively from about 11% to about 15%, and alternatively about 13%. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-dipho sphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Examples of some colorants that may be used in oral care compositions include D&C Yellow No. 10, FD&C Blue No. 1, FD&C Red No. 40, D&C Red No. 33 and combinations thereof. In certain examples, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. The composition can contain from about 2% to about 25% abrasive polishing material, alternatively from about 5% to about 20%, alternatively from about 7% to about 18%, alternatively from about 9% to about 16%, and alternatively from about 12% to about 15%. The composition can contain 10% abrasive polishing material and alternatively about 15% abrasive polishing material.

The abrasive polishing material can have a BET surface area greater than about 5 $m^2/g$, alternatively greater than about 10 $m^2/g$, alternatively greater than about 15 $m^2/g$, alternatively greater than about 18 $m^2/g$, alternatively greater than about 25 $m^2/g$, alternatively greater than about 30 $m^2/g$, alternatively greater than about 35 $m^2/g$, alternatively greater than about 40 $m^2/g$, and alternatively greater than about 50 $m^2/g$. The BET surface area of the abrasive polishing material is from about 5 $m^2/g$ to about 30 $m^2/g$, alternatively from about 10 $m^2/g$ to about 200 $m^2/g$, alternatively from about 20 $m^2/g$ to about 150 $m^2/g$, alternatively from about 25 $m^2/g$ to about 100 $m^2/g$, alternatively from about 30 $m^2/g$ to about 75 $m^2/g$, alternatively from about 35 $m^2/g$ to about 60 $m^2/g$, alternatively from about 38 $m^2/g$ to about 50 $m^2/g$, and alternatively from about 40 $m^2/g$ to about 45 $m^2/g$. The precipitated silica can have a BET surface area from about 19 $m^2/g$ to about 55 $m^2/g$ and alternatively from about 19 $m^2/g$ to about 35 $m^2/g$. The silica can have a BET surface area from about 10 $m^2/g$ to about 80 $m^2/g$, alternatively from about 20 $m^2/g$ to about 70 $m^2/g$, alternatively from about 25 $m^2/g$ to about 50 $m^2/g$, or alternatively from about 30 $m^2/g$ to about 45 $m^2/g$. BET surface area is determined by BET nitrogen absorption method of Brunaur et al., *J. Am. Chem. Soc.*, 60, 309 (1938). See also U.S. Pat. No. 7,255,852 to Gallis.

Typical abrasive polishing materials can include silicas including gels and precipitates; aluminas; phosphates including orthophosphates, polymetaphosphates, and pyrophosphates; and mixtures thereof. Specific examples include silicone microspheres such as polyorganosilsesquioxane particles, dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. In certain examples, if the oral composition or particular phase comprises a polyphosphate having an average chain length of about 4 or more, calcium containing abrasives and alumina are not preferred abrasives. In certain examples, the composition is substantially free of silica.

The composition can contain a silica abrasive. Silica abrasive polishing materials that may be used in the present invention, as well as other abrasives, generally have an average particle size ranging between about 0.1 to about 30 µm or from about 5 to about 15 µm. The abrasive can be precipitated silica or silica gels such as the silica xerogels described in Pader et al., U.S. Pat. No. 3,538,230 and DiGiulio, U.S. Pat. No. 3,862,307. Silica xerogels marketed under the trade name "Syloid" by the W.R. Grace & Company, Davison Chemical Division, Augusta, Ga. may be used. Also precipitated silica materials such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in U.S. Pat. Nos. 4,340,583; 5,589,160; 5,603,920; 5,651,958; 5,658,553; and 5,716,601.

The abrasive can include polymethyl organosiloxane particles. The types of polymethyl organosiloxane particles useful in the oral care compositions of the present invention are described in more detail in U.S. Pat. No. 9,017,647. It may be advantageous to select an abrasive containing polymethyl organosiloxane particles because they are less reactive with ingredients commonly found in oral care compositions, in including oral care actives.

The abrasive can include calcium pyrophosphate. The abrasive can include poly(methyl methacrylate), calcium carbonate, dicalcium phosphate, and/or barium sulfate.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

Flavor Aroma Display in Headspace Over
Dentifrice Slurry by GC/MS

The following three headspace sample preparation methods were developed to simulate and measure flavor display (release from oral care composition) during brushing. This is achieved by slurrying the dentifrice in water or artificial saliva and then sampling the headspace and measuring the flavor components contained in the headspace sample by GC/MS.

Headspace Sample Preparation 1: 30 min Static, HP-5 Column

One gram of dentifrice is placed into a 20-mL headspace vial (Wheaton p/n 16-2000; caps Wheaton p/n 16-0050m, Wheaton® Industries Incorporated, Millville, N.J., USA). Three mL deionized water is added. A stir bar is added, then the vial is capped and placed onto a Gerstel™ MultiPurpose Sampler MPS2 tray (VT32-20, Gerstel™ Incorporated, Linthicum, Md. USA). Each sample is incubated for 30 minutes at 37° C. with stirring at 250 rpm in a Gerstel™ MultiPurpose Sampler MPS2 tray with a Gerstel Agitator/Stirrer. One mL of the headspace is withdrawn by syringe maintained at 109° C. and injected into an Agilent 7890 gas chromatograph equipped with an HP-5MS column (30M×0.25 mm ID×0.25 µm film thickness; Agilent p/n 19091S-433) and an Agilent 5975C MSD (all from Agilent™ Technologies, Wilmington, Del., USA). The percentage of high flavor displayers in headspace after simulated brushing is calculated after analysis using this method by summing the peak areas in the chromatogram arising from high displaying flavor components and dividing by the total peak area arising from all flavor components, and expressing the result as a percentage.

Headspace Sample Preparation 2: 1 min Static, HP-FFAP Column

One gram of dentifrice is placed into a 20-mL headspace vial as above. Three mL of artificial saliva is added to each vial. The artificial saliva solution is comprised of 20 mM NaHCO3, 2.75 mM K2HPO4, 12.2 mM KH2PO4, and 15 mM NaCl at pH of 7.0 dissolved in distilled water. A stir bar is added, then the vial is capped and placed onto the MPS2 tray. Prior to GC-MS analysis, each sample, in sequence, is incubated for 1 minute at 37° C. with stirring at 400 rpm in the agitator/stirrer component of the Gerstel™ sampler. One mL of the headspace is withdrawn by syringe maintained at 109° C. and injected into an Agilent 7890 gas chromatograph equipped with an HP-FFAP column (30M×0.25 mm ID×0.25 μm film thickness; Agilent p/n 19091F-433) and an Agilent 5975C MSD.

Headspace Sample Preparation 3: 1 min SPME, HP-FFAP Column

One half gram of dentifrice is placed into a 10-mL headspace vial (Gerstel™ vial part number 093640-038-00 with Gerstel™ cap, part number 093640-040-00). One gram of 2.4 mm diameter metal mixing beads (Omni International part number 19-640, VWR International, LLC, Visalia, Calif., USA) is added, then the vial is capped and placed onto the MPS2 tray. Prior to GC-MS analysis, each sample, in sequence, receives 1.5 mL artificial saliva via syringe. The vial is vortexed at 2500 rpm for 1 minute in the mVorx component of the Gerstel™ sampler. The headspace is sampled for 15 seconds with a solid phase microextraction (SPME) fiber (triphase DVB/CAR/PDMS, 50/30 μm, Stableflex 23Ga, Supelco part number 57298-U). The SPME fiber is then desorbed for 5 minutes in the inlet of an Agilent 7890 gas chromatograph equipped with an HP-FFAP column (30M×0.25 mm ID×0.25 um film thickness; Agilent p/n 19091F-433) and an Agilent 5975C MSD. The percentage of high flavor displayers in headspace after simulated brushing is calculated after analysis using this method by summing the peak areas in the chromatogram arising from high displaying flavor components and dividing by the total peak area arising from all flavor components, and expressing the result as a percentage.

Gas Chromatographic Conditions (Used for All Headspace Over Dentifrice Slurry Sample Preparations)

Gas chromatographic conditions are as follows: Inlet temperature 250° C.; split ratio 15:1; column flow 1.4 mL helium/minute; oven temperature program 40° C. for 0.5 minute, then ramp 15° C./minute to 240° C. and hold for 1.5 minutes.

Mass Spectrometric Conditions (Used for All Headspace Over Dentifrice Slurry Sample Preparations)

Mass spectrometric conditions are as follows: Electron ionization (70 eV); transfer line temperature 250° C.; source temperature 230° C.; quadrupole temperature 150° C.; acquisition scan from mass to charge ratio of 35 to 350. Each flavor compound is identified from its retention time and mass spectral fragmentation pattern.

Quantification of Percent Flavor in Fatty Amphiphile Dentifrice by GC-MS

A 330 mg dentifrice sample is placed in a vial with 9.5 mL methanol and 0.50 mL of an internal standard solution (ISTD) containing 4 mg/mL linalool in methanol. Glass beads are added before the vial is capped and vortexed for 30 minutes at 2000 rpm. The solution is filtered through a syringe filter (PVDF 0.45 μm pore size) and injected into an Agilent 7890 gas chromatograph equipped with an HP-FFAP column (30M×0.25 mm ID×0.25 um film thickness; Agilent p/n 19091F-433) and an Agilent 5975C MSD.

A stock calibration solution is made by weighing flavor compounds into a tared, 100-mL volumetric flask, see Table 9 below for composition of the calibration stock solution. The flask is diluted to volume with methanol and stirred to dissolve. This solution is diluted 0.05:10, 0.1:10, 0.5:10, 1:10 and 2:10 in methanol to create a 5-point calibration curve. Each calibration solution also receives 0.5 mL ISTD before being diluted to volume.

TABLE 9

Composition of Calibration Stock Solution

| Flavor Compound | Concentration in Calibration Stock Solution (mg/mL) |
| --- | --- |
| beta-Pinene | 0.078 |
| Limonene | 0.159 |
| Eucalyptol | 0.323 |
| Allyl Caproate | 0.160 |
| Menthone | 0.794 |
| Menthyl Acetate | 0.645 |
| Peppermint Cyclohexanone | 0.087 |
| (−)-trans-Caryophyllene | 0.086 |
| 1-Menthol | 3.687 |
| (−)-Carvone | 0.562 |
| Delta-Damascone | 0.177 |
| Methyl Salicylate | 1.479 |
| Trans-Anethole | 0.837 |
| WS-23 | 0.089 |
| Caryophyllene Oxide | 0.114 |
| Thymol | 0.435 |
| WS-3 | 0.712 |
| Delta-Dodecalactone | 0.192 |
| WS-5 | 0.307 |
| Oxanone | 0.268 |

Chromatographic conditions are as follows: Inlet temperature 250° C.; split ratio 15:1; column flow 1.2 mL helium/minute; oven temperature program initial temperature 40° C., then 15° C./minute to 250° C. and hold for 5 minutes.

Mass spectrometric conditions are as follows: Electron ionization (70 eV); transfer line temperature 227° C.; source temperature 230° C.; quadrupole temperature 150° C.; acquisition mode scan from mass to charge ratio 35 to 350. Each flavor compound is identified from its retention time and mass spectral fragmentation pattern.

Calibration curves are obtained for each flavor compound by plotting the analyte area/ISTD area ratio versus the concentration of analyte. The percentage of each analyte in the sample is calculated as follows:

$$\text{Conc } (\% \text{ w/w}) = (y - b/m) * (10 \text{ mL/w}) * 100$$

Where y is the analyte area/ISTD area ratio, b is the y-intercept, m is the slope, and w is the sample weight in mg. Quantification of alpha pinene and iso-menthone were achieved using the quantitative values obtained from beta pinene and l-menthone quantitation and ratioing their respective peak areas.

Brookfield Viscosity Test

The viscometer is Brookfield viscometer, Model 1/2 RVT, with a Brookfield "Heliopath" stand (available from Brookfield Engineering Laboratories, Middleboro, Mass.). The spindle is a conventional "E-series" T-shaped spindle. The viscometer is placed on the Heliopath stand and leveled via spirit levels. The E spindle is attached, and the viscometer is set to 2.5 RPM while it is running. The viscosity is measured after 1 minute and the temperature is constant at 25° C. The "Brookfield Unit" in which results obtained from this method have traditionally been expressed is simply the direct readout of the instrument under standard conditions, i.e., using the "E" spindle at 2.5 RPM, or calculated equivalent.

pH Test Method

First, calibrate the Thermo Scientific Orion 320 pH meter. Do this by turning on the pH meter and waiting for 30 seconds. Then take the electrode out of the storage solution, rinse the electrode with distilled water, and carefully wipe the electrode with a scientific cleaning wipe, such as a Kimwipe®. Submerse the electrode in the pH 7 buffer and press the calibrate button. Wait until the pH icon stops flashing and press the calibrate button a second time. Rinse the electrode with distilled water and carefully wipe the electrode with a scientific cleaning wipe. Then submerse the electrode into the pH 4 buffer and wait until the pH icon stops flashing and press the measure button. Rinse the electrode with distilled water and carefully wipe with a scientific cleaning wipe. Now the pH meter is calibrated and can be used to test the pH of a solution.

The pH of the liquid medication is measured using the calibrated pH meter at ambient temperature.

Combinations

A. An oral care composition comprising: (a) at least 4% fatty amphiphile; (b) from 0.4% to 5%, by weight of the composition, total flavor component; wherein the flavor component comprises at least 14%, by weight of the flavor component, of one or more high displaying flavor components; wherein the high displaying flavor components comprise an ACD vapor pressure greater than or equal to 0.06 Torr, a $\delta_P$ less than or equal to 5.3 MPa$^{1/2}$, and a $\delta_H$ of less than or equal to 7.0 MPa$^{1/2}$.

B. An oral care composition comprising: (a) at least 4% fatty amphiphile; (b) from 0.4% to 5%, by weight of the composition, total flavor component; wherein the flavor component comprises one or more high displaying flavor components comprising: (i) from 4% to 20%, by weight of the total flavor component, anethole; (ii) from 4% to 30%, by weight of the total flavor component, menthone.

C. The oral care composition according to any one of the preceding paragraphs A-B wherein the oral care composition comprises a gel network phase comprising the fatty amphiphile and a secondary surfactant.

D. The oral care composition according to any one of the preceding paragraphs A-C wherein the flavor component comprises at least 20%, by weight of the total flavor component, of one or more high displaying flavor components, or at least 25%, or at least 30%, or at least 33%, or at least 35%, or at least 40%.

E. The oral care composition according to any one of the preceding paragraphs A-D wherein the oral care composition comprises from 30 to 90 peak area % high displayers in a headspace according to the Aroma Display in Headspace over Dentifrice Slurry by GC/MS method 3, 1 minute SPME, or 40 to 88 peak area % high displayers in a headspace, or 45 to 86 peak area % high displayers in a headspace, or 55 to 75 peak area % high displayers in a headspace.

F. The oral care composition according to any one of the preceding paragraphs A-E wherein the oral care composition comprises at least 20 peak area % of high displayers in a headspace according to the Aroma Display in Headspace over Dentifrice Slurry by GC/MS method 3, 1 minute SPME, or at least 30% peak area % high displayers in a headspace, or at least 40% peak area % high displayers in a headspace, or at least 50% peak area % high displayers in a headspace, or at least 60% peak area % high displayers in a headspace.

G. The oral care composition according to any one of the preceding paragraphs A-F wherein the one or more high displaying flavor components are selected from the group consisting of ethyl methyl butyrate, isoamyl acetate, alpha-pinene, sabinene, beta-pinene, myrcene, eucalyptol, alpha-terpinene, beta-phellandrene, cis-ocimene, trans-ocimene, l-limonene, terpineolene, g-terpinene, melonal, dihydroanethole, isomenthone, menthone, peppermint cyclohexanone, cyclohexyl ethyl acetate, tetrahydrocarvone, d-dihydrocarvone, linalool, sabinene hydrate, citral, l-menthyl acetate, menthyl acetate, anethole, trans anethole, and combinations thereof.

H. The oral care composition according to any one of the preceding paragraphs A-G wherein the one or more high displaying flavor components are selected from the group consisting of anethole, eucalyptol, limonene, menthone, alpha pinene, beta pinene, ethyl methyl butyrate, and combinations thereof.

I. The oral care composition according to any one of the preceding paragraphs A-H wherein the flavor component further comprises from 0.1% to 10%, by weight of the total flavor component, ethyl methyl butyrate, or from 0.25% to 7%, or from 0.5% to 5%, or from 1% to 3%.

J. The oral care composition according to any one of the preceding paragraphs A-I wherein the flavor component further comprises 0.05% to 5% alpha pinene, by weight of the total flavor component, or from 0.15% to 3%, or from 0.25% to 1.5%, or from 0.5% to 1%.

K. The oral care composition according to any one of the preceding paragraphs A-J wherein the flavor component further comprises 0.05% to 5% beta pinene, by weight of the total flavor component, or from 0.15% to 3%, or from 0.25% to 1.5%, or from 0.5% to 1%.

L. The oral care composition according to any one of the preceding paragraphs A-K further comprising one or more non-high displaying flavor components selected from the group consisting of l-menthol, methyl salicylate, carvone, and combinations thereof.

M. The oral care composition according to paragraph L comprising from 0.1% to about 3% of non-high displaying flavor components, by weight of the composition, or from 0.25% to 2.5%, or from 0.5% to 2%, or from about 0.7% to 1.5%.

N. The oral care composition according to any one of the preceding paragraphs A-M wherein the composition comprises from 10% to 50% l-menthol, by weight of the total flavor component, or from 20% to 45%, or from about 25% to 40%, or from 32% to 38%.

O. The oral care composition according to any one of the preceding paragraphs A-N wherein the composition comprises from 5% to 50% methyl salicylate, by weight of the total flavor component, or from 10% to 40%, or from 15% to 35%, or from 20% to 30%.

P. The oral care composition according to any one of the preceding paragraphs A-O wherein the flavor component further comprises from 0.25% to 7%, by weight of the flavor component, eucalyptol, or from 0.5% to 5%, or from 1% to 3%.

Q. The oral care composition according to any one of the preceding paragraphs A-P wherein the flavor component further comprises from 0.25% to 7%, by weight of the total flavor component, limonene, or from 0.5% to 5%, or from about 1% to about 3%.

R. The oral care composition according to any one of the preceding paragraphs A-Q wherein the fatty amphiphile comprises a fatty alcohol selected from the group consisting of cetyl alcohol, stearyl alcohol, and combinations thereof.

S. The oral care composition according to any one of the preceding paragraphs A-Q wherein the composition further comprises from about 15% to about 95%, by weight of the composition, water, or from about 25% to about 70% water, or from about 30% to about 50% water, or from about 32% to about 45% water.

T. The oral care composition according to any one of the preceding paragraphs A-S wherein the composition further comprises from 1% to 8%, by weight of the composition, potassium nitrate, or from 4% to 6%, or 5%.

U. The oral care composition according to any one of the preceding paragraphs A-S wherein the secondary surfactant comprises sodium lauryl sulfate.

V. The oral care composition according to paragraphs A-U wherein the composition further comprises a peroxide compounded selected from the group consisting of hydrogen peroxide, urea peroxide, calcium peroxide, sodium peroxide, zinc peroxide, polyvinylpyrrolidone peroxide complex or combinations thereof.

W. The oral care composition according to paragraph V wherein the composition comprises from about 0.01% to about 6% peroxide, or from about 0.05% to about 3% peroxide, or from about 0.1% to about 1% peroxide.

X. The oral care composition according to paragraphs A-W further comprising from about 2% to about 25% abrasive, or from about 5% to about 20% abrasive, or from about 7% to about 18% abrasive, or from about 9% to about 16% abrasive.

Y. The oral care composition according to paragraphs A-X further comprising a fluoride ion source selected from the group consisting of stannous fluoride, sodium fluoride, potassium fluoride, amine fluoride, sodium monofluorophosphate, indium fluoride, amine fluoride, and combinations thereof.

Z. The oral care composition according to paragraphs A-Y wherein the composition comprises from 0.8% to 4%, by weight of the oral care composition, flavor component, or from about 1% to 3.5%, or from 1.5% to 3%.

AA. The oral care compositions according to paragraphs A-Z wherein the composition comprises from about 5% to about 15%, by weight of the total flavor component, anethole, or from 7% to 13%, or from about 9% to about 12%.

BB. The oral care compositions according to paragraphs A-AA wherein the composition comprises from 5% to 20%, by weight of the total flavor component menthone, or from 7% to about 16%, or from 10% to 14%.

CC. The oral care compositions according to paragraphs A-BB wherein the composition comprises at least 5%, by weight of the composition, fatty amphiphile, or at least 7.5%, or at least 10%, or at least 11%, or at least 13%.

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a. at least 4% of a cold dispersible fatty amphiphile, the cold dispersible fatty amphiphile comprising:
      i. from about 70% to about 85%, by weight of the cold dispersible fatty amphiphile, of fatty alcohol,
      ii. from about 10% to about 15%, by weight of the cold dispersible fatty amphiphile, of surfactant, and
      iii. from about 8% to about 15%, by weight of the cold dispersible fatty amphiphile, of sodium acrylate/sodium acryloyl dimethyl taurate copolymer;
   b. from about 0.4% to about 5%, by weight of the composition, total flavor components;
      wherein the total flavor components comprise (i) from about 20% to about 38%, by weight of the total flavor components, of one or more high displaying flavor components selected from the group consisting of ethyl methyl butyrate, isoamyl acetate, alpha-pinene, sabinene, beta-pinene, myrcene, eucalyptol, alpha-terpinene, beta-phellandrene, cis-ocimene, trans-ocimene, l-limonene, terpineolene, g-terpinene, melonal, dihydroanethole, isomenthone, menthone, peppermint cyclohexanone, cyclohexyl ethyl acetate, tetrahydrocarvone, d-dihydrocarvone, linalool, sabinene hydrate, l-menthyl acetate, menthyl acetate, anethole, trans anethole, and combinations thereof; and (ii) from about 62% to about 80%, by weight of the total flavor components, of one or more non-high displaying flavor components selected from the group consisting of menthol, methyl salicylate, and carvone;

wherein the high displaying flavor components comprise a vapor pressure greater than or equal to 0.06 Torr, a polarity parameter, $\delta_P$, of less than or equal to 5.3 MPa$^{1/2}$, and a hydrogen bonding parameter, $\delta_H$, of less than or equal to 7.0 MPa$^{1/2}$.

2. The oral care composition of claim 1 wherein the total flavor components comprise (i) from about 20% to about 30%, by weight of the total flavor components, of one or more high displaying flavor components.

3. The oral care composition of claim 1 wherein the oral care composition comprises from about 40 to about 88 peak area % high displayers in a headspace according to Flavor Aroma Display in Headspace over Dentifrice Slurry by a combination of gas chromatography and mass spectrometry with 1 minute solid phase microextraction.

4. The oral care composition of claim 1 wherein the oral care composition comprises at least 45 peak area % of high displayers in a headspace according to Flavor Aroma Display in Headspace over Dentifrice Slurry by a combination of gas chromatography and mass spectrometry with 1 minute solid phase microextraction.

5. The oral care composition of claim 1 wherein the one or more high displaying flavor components are selected from the group consisting of anethole, eucalyptol, l-limonene, menthone, alpha pinene, beta pinene, ethyl methyl butyrate, and combinations thereof.

6. An oral care composition comprising:
  a. at least 4% of a cold dispersible fatty amphiphile, the cold dispersible fatty amphiphile comprising:
    i. from about 70% to about 85%, by weight of the cold dispersible fatty amphiphile, of fatty alcohol,
    ii. from about 10% to about 15%, by weight of the cold dispersible fatty amphiphile, of surfactant, and
    iii. from about 8% to about 15%, by weight of the cold dispersible fatty amphiphile, of sodium acrylate/sodium acryloyl dimethyl taurate copolymer;
  b. from about 0.4% to about 5%, by weight of the composition, total flavor components;
  wherein the total flavor components comprise:
    i. from about 20% to about 38%, by weight of the total flavor components, of one or more high displaying flavor components, the one or more high displaying flavor components comprising from about 4% to about 20%, by weight of the total flavor components, anethole; and from about 4% to about 30%, by weight of the total flavor components, menthone; and
    ii. from about 1% to about 70%, by weight of the total flavor components, menthol;
  wherein the high displaying flavor components comprise a vapor pressure greater than or equal to 0.06 Torr, a polarity parameter, $\delta_P$, of less than or equal to 5.3 MPa$^{1/2}$, and a hydrogen bonding parameter, $\delta_H$, of less than or equal to 7.0 MPa$^{1/2}$.

7. The oral care composition of claim 6 wherein the total flavor components further comprise from about 0.1% to about 10%, by weight of the total flavor components, ethyl methyl butyrate.

8. The oral care composition of claim 6 wherein the total flavor components further comprise about 0.05% to about 5%, by weight of the total flavor components, alpha pinene.

9. The oral care composition of claim 6 wherein the total flavor components further comprise about 0.05% to about 5%, by weight of the total flavor components, beta pinene.

10. The oral care composition of claim 6 wherein the total flavor components further comprise l-menthol, methyl salicylate, carvone, or combinations thereof.

11. The oral care composition of claim 10 wherein the composition comprises from about 10% to about 50%, by weight of the total flavor components, l-menthol.

12. The oral care composition of claim 10 wherein the composition comprises from about 5% to about 50%, by weight of the total flavor components, methyl salicylate.

13. The oral care composition of claim 10 wherein the total flavor components further comprise from about 0.25% to about 7%, by weight of the total flavor components, eucalyptol.

14. The oral care composition of claim 6 wherein the total flavor components further comprise from about 0.5% to about 5%, by weight of the total flavor components, limonene.

15. An oral care composition comprising:
  a. a gel network phase comprising at least 4% of a cold dispersible fatty amphiphile, the cold dispersible fatty amphiphile comprising:
    i. from about 70% to about 85%, by weight of the cold dispersible fatty amphiphile, of fatty alcohol,
    ii. from about 10% to about 15%, by weight of the cold dispersible fatty amphiphile, of surfactant, and
    iii. from about 8% to about 15%, by weight of the cold dispersible fatty amphiphile, of sodium acrylate/sodium acryloyl dimethyl taurate copolymer;
  b. from about 2% to about 25%, by weight of the composition, abrasive; and
  c. a fluoride ion source selected from the group consisting of stannous fluoride, sodium fluoride, potassium fluoride, amine fluoride, sodium monofluorophosphate, indium fluoride, amine fluoride, and combinations thereof; wherein the fluoride ion source provides a fluoride ion concentration from about 0.005% to about 2.0%, by weight of the composition;
  d. from about 1% to about 90% water;
  e. from about 0.4% to about 5%, by weight of the composition, total flavor components;
  wherein the flavor components comprise (i) from about 20% to about 38%, by weight of the total flavor components, of one or more high displaying flavor components selected from the group consisting of anethole, eucalyptol, limonene, menthone, ethyl methyl butyrate, and combinations thereof; and (ii) from about 1% to about 70%, by weight of the total flavor components, of menthol or from about 1% to about 60%, by weight of the total flavor components, of methyl salicylate;
  wherein the high displaying flavor components comprise a vapor pressure greater than or equal to 0.06 Torr, a polarity parameter, $\delta_P$, of less than or equal to 5.3 MPa$^{1/2}$, and a hydrogen bonding parameter, $\delta_H$, of less than or equal to 7.0 MPa$^{1/2}$.

16. The oral care composition of claim 15 wherein the fatty amphiphile comprises a fatty alcohol selected from the group consisting of cetyl alcohol, stearyl alcohol, and combinations thereof.

17. The oral care composition of claim 15 wherein the composition further comprises from about 1% to about 8%, by weight of the composition, potassium nitrate.

18. The oral care composition of claim 15 wherein the composition further comprises from about 0.5% to about 10%, by weight of the composition, of a peroxide compound.

* * * * *